(12) United States Patent
Laskowitz et al.

(10) Patent No.: US 7,319,092 B2
(45) Date of Patent: Jan. 15, 2008

(54) METHODS OF SUPPRESSING MICROGLIAL ACTIVATION

(75) Inventors: Daniel T. Laskowitz, Chapel Hill, NC (US); William D. Matthew, Durham, NC (US); Michael McMillian, Rareton, NJ (US)

(73) Assignee: Cognosci, Inc, Research Triangle Park, NC (US)

( * ) Notice: Subject to any disclaimer, the term of this patent is extended or adjusted under 35 U.S.C. 154(b) by 0 days.

(21) Appl. No.: 11/091,336

(22) Filed: Mar. 29, 2005

(65) Prior Publication Data

US 2006/0008797 A1 Jan. 12, 2006

Related U.S. Application Data

(60) Division of application No. 09/957,909, filed on Sep. 21, 2001, now Pat. No. 7,205,280, which is a continuation-in-part of application No. 09/260,430, filed on Mar. 1, 1999, now abandoned.

(60) Provisional application No. 60/077,551, filed on Mar. 11, 1998.

(51) Int. Cl.
A61K 38/00 (2006.01)

(52) U.S. Cl. .............................. 514/13; 514/2; 514/21; 530/300; 530/326

(58) Field of Classification Search ...................... None
See application file for complete search history.

(56) References Cited

U.S. PATENT DOCUMENTS

| 4,902,505 | A | | 2/1990 | Pardridge et al. ........... 424/85.7 |
|---|---|---|---|---|
| 5,017,566 | A | * | 5/1991 | Bodor ......................... 514/58 |
| 5,168,045 | A | * | 12/1992 | Dyer et al. ................. 435/7.92 |
| 5,182,364 | A | | 1/1993 | Dyer et al. .................. 530/324 |
| 5,204,327 | A | | 4/1993 | Kiyota et al. .................. 514/12 |
| 5,473,039 | A | | 12/1995 | Dyer et al. .................. 530/324 |
| 5,604,198 | A | | 2/1997 | Poduslo et al. ................. 514/6 |
| 5,686,416 | A | | 11/1997 | Kozarich et al. ............. 514/15 |
| 6,245,751 | B1 | | 6/2001 | Crutcher et al. |
| 6,605,588 | B1 | | 8/2003 | Lees et al. ..................... 514/2 |

FOREIGN PATENT DOCUMENTS

| WO | WO 92/10512 | 6/1992 |
|---|---|---|
| WO | WO 95/06456 | 3/1995 |
| WO | WO 97/14437 | 4/1997 |
| WO | WO 98/01101 | 1/1998 |
| WO | WO 99/08701 A1 | 2/1999 |
| WO | WO 99/45950 | 9/1999 |
| WO | WO 2003/026479 A2 | 4/2003 |
| WO | WO 2003/026479 A3 | 4/2003 |

OTHER PUBLICATIONS

Laskowitz et al., "Downregulation of Microglial Activation by Apolipoprotein E and ApoE-Mimetic Peptide", Experimental Neurology, 167:74-85 (2001).
Yan et al., "Two-amino acid molecular switch in an epithelial morphogen that regulates binding to two distinct receptors", Science, 290:523-527 (2000).
Voet et al., Biochemistry, John Wiley & Sons, Inc., 126-128 and 228-234 (1990).
Mickle, J.E. et al., "Genotype-phenotype relationships in cystic fibrosis", Med. Clin. North Am., 84(3):597-607 (May 2000).
A. Cardin et al., "Inhibition of Lymphocyte Proliferation b Synthetic Peptides Homologous to Human Plasma Apolipoproteins B and E" Biochemical and Biophysical Research Communications, 154:741-745 (Jul. 1998).
A. Lalazar et al., "Site-specific Mutagenesis of Human Apolipoprotein E", The Journal of Biological Chemistry, 263:3542-3545 (1988).
Bowie et al., "Deciphering the message in protein sequences: tolerance to amino acid substitutions", Science, 247:1306-1310 (1990).
C. Dyer et al., "A Synthetic Peptide Mimic of Plasma Apolipoprotein E That Binds the LDL Receptor", the Journal of Biological Chemistry, 266:22803-22806 (Dec. 1991).
C. Dyer et al., "Only Multimers of a Synthetic Peptide of Human Apolipoprotein E Are Biologically Active", The Journal of Biological Chemsitry, 266:15009-15015 (1991).
Christie et al., "Expression of the Very Low-Density Lipoprotein Receptor (VLDL-r), an Apolipoprotein-E Receptor, in the Central Nervous System and in Alzheimer's Disease", Journal of Neuropathology and Experimental Neurolog, 55(4):491-498 (1996).
D. Laskowitz et al., "Apolipotrotein E Suppresses Glial Cell Secretion of TNF-α", Journal of Neuroimmunology, 76:70-74 (1997).
D. Laskowitz et al., "Apolipoprotein E-Deficient Mice Have Increased Susceptibility to Focal Cerebral Ischemia", Journal of Cerebral Flow and Metabolism, 17:753-758 (1997).
Holtzman et al., "Low density lipoprotein receptor-related protein mediates apolipoprotein E-dependent neurite outgrowth in a central nervous system-derived neuronal cell line", Proc. Natl. Acad. Sci. USA, 92:9480-9484 (1995).
International Search Report for PCT/US99/05221 (mailed Nov. 3, 1999).

(Continued)

*Primary Examiner*—Lorraine Spector
*Assistant Examiner*—Gregory S. Emch
(74) *Attorney, Agent, or Firm*—Cooley Godward Kronish, LLP

(57) ABSTRACT

Methods of suppressing the activation of microglial cells in the Central Nervous System (CNS), methods of ameliorating or treating the neurological effects of cerebral ischemia or cerebral inflammation, and methods of combating specific diseases that affect the CNS by administering a compound that binds to microglial receptors and prevents or reduces microglial activation are described. Also described are methods of screening compounds for the ability to suppress or reduce microglial activation.

5 Claims, 7 Drawing Sheets

OTHER PUBLICATIONS

K. Crutcher et al., "Neurite Degeneration Elicited by Apolipoprotein E Peptides", Experimental Neurology, 130:120-126 (1994).

K. Weisgraber et al., "The Receptor-binding Domain of Human Apolipoprotein E", Journal of Biological Chemistry, 258:12348-12354 (1983).

L. Dong et al., "Enhanced Binding Activity of an Apolipoprotein E. Mutant, APO E5 to LDL Receptors on Human Fibroblasts", Biochemical and Biophysical Research Communications, 168:409-414 (Apr. 1990).

L. Dong et al., "Site-Directed Mutagenesis of an Apolipoprotein E. Mutant, APO E5 ($GLU_3 \rightarrow LYS$) and its Binding to Low Density Lipoprotein Receptors", Biochemical and Biophysical Research Communications, 187:1180-1186 (Sep. 1992).

Laskowitz et al., "Apolipoprotein E and the CNS Response to Injury", J. Cereb. Blood Flow Metab., 18(5):465-471 (1998).

Laskowitz et al., "Endogenous apolipoprotein E suppresses LPS-stimulated microglial nitric oxide production", Clinical Neuroscience and Neuropathology, NeuroReport, 9(4):615-618 (1998).

M. Clay et al., "Localization of a Domain in Apolipoprotein E with Both Cytostatic and Cytotoxic Activity", Biochemistry, 34:11142-11151 (1995).

Pardridge, W.M., "Chapter 12: Blood-brain barrier peptide transport and peptide delivery to the brain, Peptide-based drug design", Ed. Taylor et al., American Chemical Society, 265-296 (1995).

R. Mrak et al., "Glial Cytokines in Alzheimer's Disease: Review and Pathogenic Implications", Hum. Pathol., 26:816-823 (Aug. 1995).

S. Barger et al., "Microglial Activation by Alzheimer Amyloid Precursor Protein and Modulation by Apolipoprotein E", Nature, 388:878-881 (Aug. 1997).

T. Innerarity et al., "Binding of Arginine-rich (E) Apoprotein after Recombination with Phospholipid Vesicles to the Low Density Lipoprotein Receptors of Fibroblast", The Journal of Biological Chemistry, 254:4186-4190 (1979).

Vitek et al., "Modulation of Nitric Oxide Production in Human Macrophages by Apolipoprotein-E and Amyloid-Beta Peptide", Biochemical and Biophysical Research Communications, 240-391 (1997).

Zielasek et al., Advances in Neuroimmunology, 6(2):191-22 (1996).

Misra et al., "Apolipoprotein E and Mimetic Peptide Initiate A Calcium-dependent Signaling Response in Macrophages", Jour. Leukocyte Bio., 70:677-683 (2001).

Aono et al., "Protective Effects of Peptides Corresponding to the Receptor Binding Region of Apolipoprotein E on NMDA Excitotoxicity in Primary Neuronol-Glial Cultures", Trip Report: 31st Annual Meeting of the Society for Neuroscience, San Diego, California (Nov. 10-15, 2001).

Benazzouz, A., et al., "Riluzole Prevents MPTP-induced Parkinsonism in the Rhesus Monkey: A Pilot Study," Eur. J. Pharmacol. 284:299-307 (1995).

Champe et al., "IV. Tertiary Structure of Globular Proteins," "V. Quaternary Structure of Proteins," "VI Denaturation of Proteins," and "VII. Protein Misfolding," pp. 18-21 in Lippincott's Illustrated Reviews: Biochemistry, 3rd Ed. Lippincott Williams & Wilkins, Philadelphia, Pennsylvania, USA (2005).

Chen et al., "Motor and Cognitive Deficits in Apolipoprotein E Deficient Mice After Closed Head Injury," Neuroscience 80:1255-1262 (1997).

Gordon, I., et al., "Derangement in Stress Response of Apolipoprotein E-deficient Mice," Neuroscience Letters 206:212-214 (1996).

Jordan et al., "Isoform-Specific Effect of Apolipoprotein E on Cell Survival and β-Amyloid-induced Toxicity in Rat Hippocampal Pyramidal Neuronal Cultures," J. Neurosci. 18:195-204 (1998).

Marzolo, M., et al., "Expression of α2-Macroglobulin Receptor/Low Density Lipoprotein Receptor-Related Protein (LRP) in Rat Microglial Cells," J. Neurosci. Res. 60:401-411 (2000).

Tolar, M., et al., "Truncated Apolipoprotein E (ApoE) Causes Increased Intracellualr Calcium and May Mediate ApoE Neurotoxicity," J. Neuroscience 19(16): 7100-7110 (1999).

Ludwig, "Supplementary European Search Report," 3 pages, from EP Appl. No. 02775888.7, European Patent Office, Munich, Germany (mailed Mar. 9, 2007).

\* cited by examiner

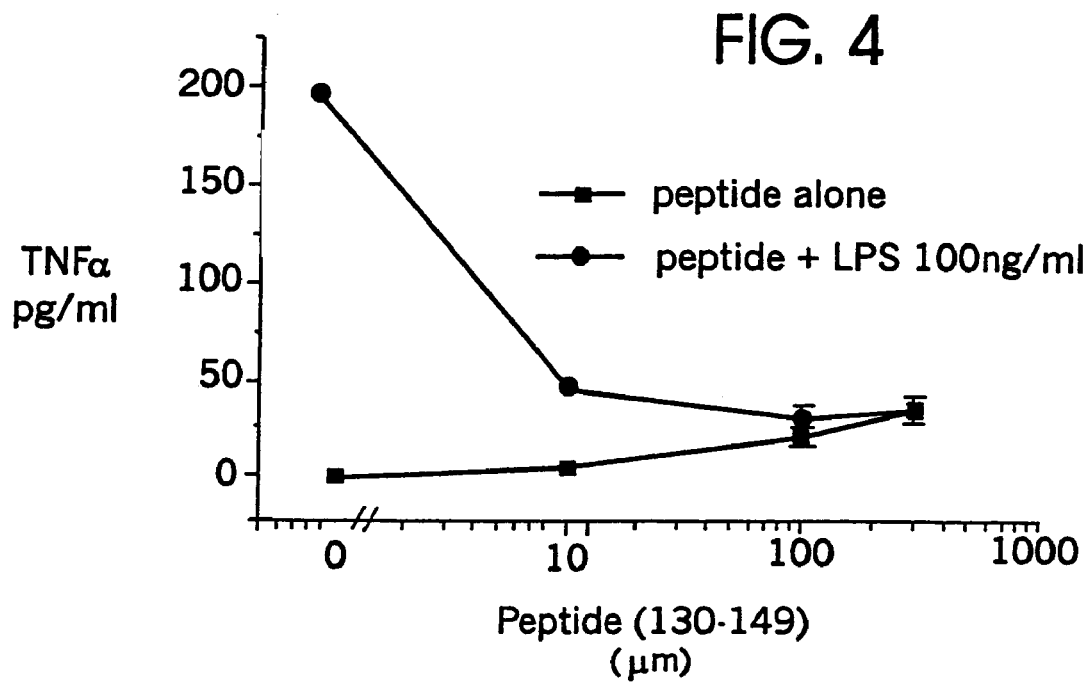
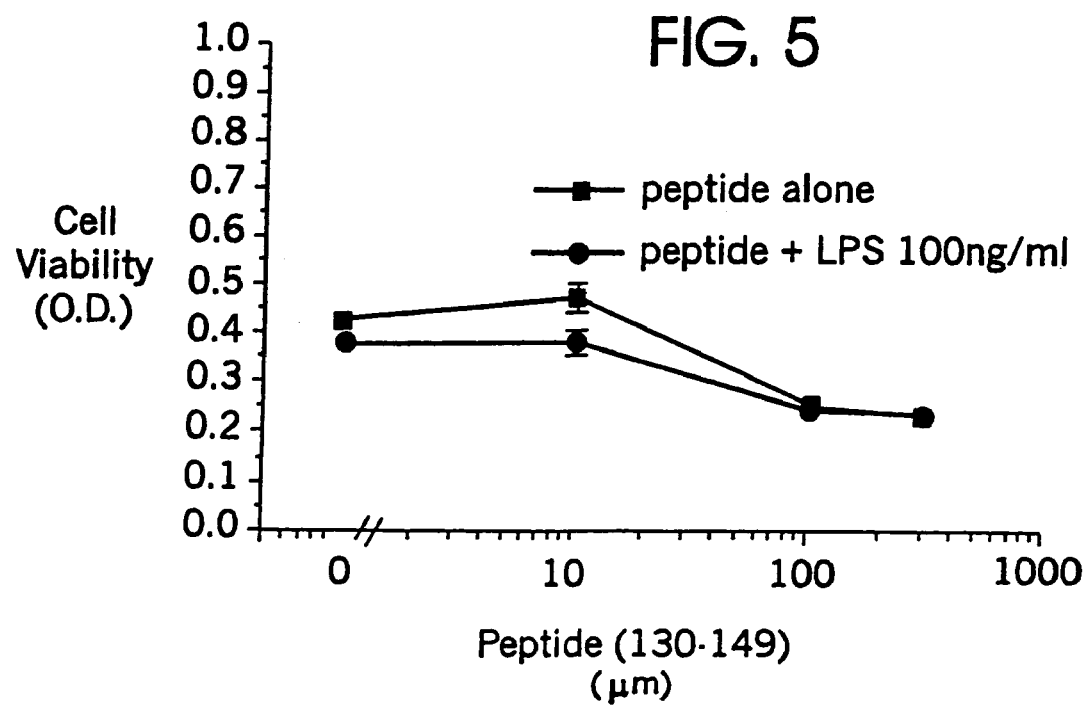

SEQUENCE LISTING

<160> NUMBER OF SEQ ID NOS: 10

<210> SEQ ID NO 1
<211> LENGTH: 16
<212> TYPE: PRT
<213> ORGANISM: Artificial Sequence
<220> FEATURE:
<223> OTHER INFORMATION: fragment of ApoE containing LDL receptor
      binding site

```
<400> SEQUENCE: 1

His Leu Arg Lys Leu Arg Lys Arg Leu Leu Arg Asp Ala Asp Asp Leu
 1               5                  10                  15

<210> SEQ ID NO 2
<211> LENGTH: 9
<212> TYPE: PRT
<213> ORGANISM: Artificial Sequence
<220> FEATURE:
<223> OTHER INFORMATION: fragment of ApoE containing LDL receptor
      binding site

<400> SEQUENCE: 2

Leu Arg Lys Leu Arg Lys Arg Leu Leu
 1               5

<210> SEQ ID NO 3
<211> LENGTH: 18
<212> TYPE: PRT
<213> ORGANISM: Artificial Sequence
<220> FEATURE:
<223> OTHER INFORMATION: fragment of ApoE containing LDL receptor
      binding site

<400> SEQUENCE: 3

Leu Arg Lys Leu Arg Lys Arg Leu Leu Leu Arg Lys Leu Arg Lys Arg
 1               5                  10                  15

Leu Leu

<210> SEQ ID NO 4
<211> LENGTH: 31
<212> TYPE: PRT
<213> ORGANISM: Artificial Sequence
<220> FEATURE:
<223> OTHER INFORMATION: fragment of ApoE containing LDL receptor
      binding site

<400> SEQUENCE: 4

Thr Glu Glu Leu Arg Val Arg Leu Ala Ser His Leu Arg Lys Leu Arg
 1               5                  10                  15

Lys Arg Leu Leu Arg Asp Ala Asp Asp Leu Gln Lys Arg Leu Ala
                20                  25                  30

<210> SEQ ID NO 5
<211> LENGTH: 31
<212> TYPE: PRT
<213> ORGANISM: Artificial Sequence
<220> FEATURE:
<223> OTHER INFORMATION: fragment of ApoE containing LDL receptor
      binding site

<400> SEQUENCE: 5

Thr Glu Glu Leu Arg Val Arg Leu Ala Ser His Leu Arg Lys Leu Arg
 1               5                  10                  15

Lys Arg Leu Leu Arg Asp Ala Asp Asp Leu Gln Lys Cys Leu Ala
                20                  25                  30

<210> SEQ ID NO 6
<211> LENGTH: 20
<212> TYPE: PRT
<213> ORGANISM: Artificial Sequence
<220> FEATURE:
<223> OTHER INFORMATION: fragment of ApoE containing LDL receptor
      binding site
```

```
-continued

<400> SEQUENCE: 6

Thr Glu Glu Leu Arg Val Arg Leu Ala Ser His Leu Arg Lys Leu Arg
 1               5                  10                  15

Lys Arg Leu Leu
            20

<210> SEQ ID NO 7
<211> LENGTH: 31
<212> TYPE: PRT
<213> ORGANISM: Artificial Sequence
<220> FEATURE:
<223> OTHER INFORMATION: fragment of ApoE containing LDL receptor
      binding site

<400> SEQUENCE: 7

Thr Glu Glu Leu Arg Val Arg Leu Ala Arg His Leu Arg Lys Leu Arg
 1               5                  10                  15

Lys Arg Leu Leu Arg Asp Ala Asp Asp Leu Gln Lys Arg Leu Ala
            20                  25                  30

<210> SEQ ID NO 8
<211> LENGTH: 31
<212> TYPE: PRT
<213> ORGANISM: Artificial Sequence
<220> FEATURE:
<223> OTHER INFORMATION: fragment of ApoE containing LDL receptor
      binding site

<400> SEQUENCE: 8

Thr Glu Glu Leu Arg Val Arg Leu Ala Arg His Leu Arg Lys Leu Arg
 1               5                  10                  15

Lys Arg Leu Leu Arg Asp Ala Asp Asp Leu Gln Lys Cys Leu Ala
            20                  25                  30

<210> SEQ ID NO 9
<211> LENGTH: 20
<212> TYPE: PRT
<213> ORGANISM: Artificial Sequence
<220> FEATURE:
<223> OTHER INFORMATION: fragment of ApoE containing LDL receptor
      binding site

<400> SEQUENCE: 9

Thr Glu Glu Leu Arg Val Arg Leu Ala Arg His Leu Arg Lys Leu Arg
 1               5                  10                  15

Lys Arg Leu Leu
            20

<210> SEQ ID NO 10
<211> LENGTH: 17
<212> TYPE: PRT
<213> ORGANISM: Artificial Sequence
<220> FEATURE:
<223> OTHER INFORMATION: fragment of ApoE containing LDL receptor
      binding site

<400> SEQUENCE: 10

Leu Arg Val Arg Leu Ala Ser His Leu Arg Lys Leu Arg Lys Arg Leu
 1               5                  10                  15

Leu
```

METHODS OF SUPPRESSING MICROGLIAL ACTIVATION

RELATED APPLICATION INFORMATION

This application is a divisional application of U.S. Application Ser. No. 09/957,909, filed Sep. 21, 2001, now U.S. Pat. No. 7,205,280, which is a continuation-in-part of U.S. patent application Ser. No. 09/260,430, filed Mar. 1, 1999, now abandoned, which in turn claims the benefit of U.S. Provisional Application No. 60/077,551, filed 11 Mar. 1998, the disclosures of which are incorporated by reference herein in their entirety.

GOVERNMENT SUPPORT

This invention was made with Government support under NIH grants NS368087-01A2, K08NS01949, and RO3 AG16507-01. The Government has certain rights to this invention.

FIELD OF THE INVENTION

The present invention relates to method of suppressing the activation of microglial cells in the Central Nervous System (CNS), methods of reducing or suppressing the activation of glial or microglial cells, methods of ameliorating or treating the neurological effects of cerebral ischemia or cerebral inflammation, methods of combating specific diseases that affect the CNS by administering a compound that binds to microglial receptors and prevents or reduces microglial activation, and methods of screening compounds for the ability to prevent or reduce microglial activation.

BACKGROUND OF THE INVENTION

The Central Nervous System (CNS) has long been considered to be a site of relative immune privilege. However, it is increasingly recognized that CNS tissue injury in acute and chronic neurological disease may be mediated by the CNS inflammatory response. The CNS inflammatory response is primarily mediated by inflammatory cytokines.

Apolipoprotein E (ApoE) is a 299 amino acid lipid-carrying protein with a known sequence (Rall et al., *J. Biol. Chem.* 257:4174 (1982); McLean et al., *J. Biol. Chem.* 259:6498 (1984). The complete gene for human ApoE has also been sequenced (Paik et al., *Proc. Natl. Acad. Sci. USA* 82:3445 (1985). ApoE sequences from at least ten species have been determined, and show a high degree of conservations across species, except at the amino and carboxyl termini. Weisgraber, *Advances in Protein Chemistry* 45:249 (1994).

Human ApoE is found in three major isoforms: ApoE2, ApoE3, and ApoE4; these isoforms differ by amino acid substitutions at positions 112 and 158. The most common isoform is ApoE3, which contains cysteine at residue 112 and arginine at residue 158; ApoE2 is the least common isoform and contains cysteine at residues 112 and 158; ApoE4 contains arginine at residues 112 and 158. Additional rare sequence mutations of human ApoE are known (see, e.g, Weisgraber, *Advances in Protein Chemistry* 45:249 (1994),at page 268-269). The presence of ApoE4 has been associated with risk of developing sporadic and late-onset Alzheimer's disease (Strittmatter et al., *Proc. Natl. Acad. Sci. USA* 90:1977-1980 (1993)).

ApoE plays a role in cholesterol metabolism and has also been reported to have immunomodulatory properties. It is secreted by macrophages after peripheral nerve injury and by astrocytes and oligodendrocytes (glial cells) after Central Nervous System (CNS) injury.

SUMMARY OF THE INVENTION

The present invention is based on the finding that microglial activation can be reduced or suppressed using peptides that comprise the receptor binding site sequence of Apolipoprotein E. Thus, the present invention provides methods and compositions for treating CNS disease states in which glial or microglial activation occurs, and in which glial or microglial activation contributes to the deleterious signs and/or symptoms associated with the specific disease state.

The present invention is further based upon the identification of the aforesaid receptor as a high affinity Apolipoprotein E receptor, with the binding characteristics of the LRP/α2M receptor.

In view of the foregoing, a first aspect of the present invention is a method of suppressing glial or microglial activation in a mammal by administering a compound that binds to glial or microglial cells at the LRP/α2M receptor (the receptor bound by a peptide of SEQ ID NO:3 or SEQ ID NO:6). The compound is administered in an amount that reduces glial or microglial activation compared to activation that which would occur in the absence of the compound.

A further aspect of the present invention is a method of ameliorating symptoms associated with CNS inflammation by administering a compound that binds to glial or microglial cells at the LRP/α2M receptor (the receptor bound by a peptide of SEQ ID NO:3 or SEQ ID NO:6).

A further aspect of the present invention is a method of ameliorating symptoms associated with CNS ischemia in a subject, by administering a compound that binds to glial or microglial cells at the LRP/α2M receptor (the receptor bound by a peptide of SEQ ID NO:3 or SEQ ID NO:6) in a treatment effective amount.

A further aspect of the present invention is a method of treating cerebral ischemia or inflammation of the CNS by administering a LRP/α2M receptor ligand, such as peptide comprising SEQ ID NO:3 or SEQ ID NO:6.

A further aspect of the present invention is a therapeutic peptide of SEQ ID NO: 3, or a dimer of two peptides wherein each peptide comprises SEQ ID NO:2, or a peptide of SEQ ID NO:6, and pharmaceutical compositions thereof.

A further aspect of the present invention is a method of screening a compound for the ability to suppress glial or microglial activation by incubating an activated glial or microglial cell culture with the compound, and then measuring a marker of microglial activation such as nitric oxide.

A further aspect of the present invention is a method of screening a compound for the ability to suppress glial or microglial activation, by pre-incubating a glial or microglial cell culture with the compound; incubating the cell culture with a known activator of glia or microglia; and then measuring a marker of glial or microglial activation.

A further aspect of the present invention is a method of screening a test compound for the ability to suppress glial or microglial activation, by determining whether the compound binds to glia or microglia at the same receptor to which peptides of SEQ ID NO:3 or SEQ ID NO:6 bind (that is, the LRP/α2M receptor).

A further aspect of the present invention is a method of suppressing macrophage activation in a mammalian subject, by administering a compound that binds to macrophage cells at the LRP/α2M receptor (the receptor bound by a peptide of SEQ ID NO:3 or SEQ ID NO:6).

A further aspect of the present invention is a method of treating atherosclerosis or of reducing the formation of atherosclerotic plaques, comprising administering a compound that binds to macrophage cells at the LRP/α2M receptor (the receptor bound by a peptide of SEQ ID NO:3 or SEQ ID NO:6).

BRIEF DESCRIPTION OF THE DRAWINGS

FIG. 4 graphs production of TNFα(picogram/ml) by microglia primary cultures from ApoE-deficient mice after addition of peptides of SEQ ID NO:6 (squares), or addition of peptides of SEQ ID NO:6 and LPS (100 ng/ml) (circles). Peptides were added in doses of 10 μM, 100 μM and 1000 μM.

FIG. 5 is a graph of the optical density of cell cultures, as a measure of cell viability. Cultures of microglia from ApoE-deficient mice were exposed to either peptides of SEQ ID NO:6 (squares), or peptides of SEQ ID NO:6 and LPS (100 ng/mil) (circles). Peptides were added in doses of 10 μM, 100 μM and 1000 μM.

DETAILED DESCRIPTION OF THE INVENTION

Figure 1:
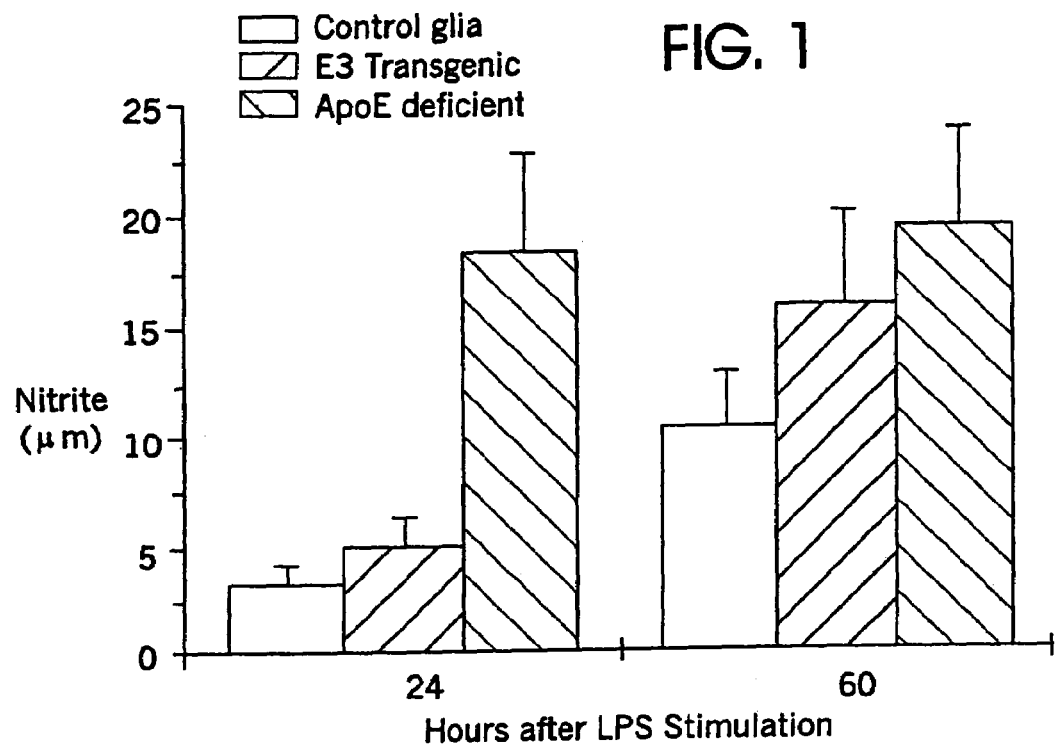
FIG. 1 graphs the production of nitrite by cultures of glial cells from ApoE-deficient mice (solid bar), ApoE3transgenic mice (hatched bar), and control mice (white bar), after exposure to lipopolysaccharide (LPS). Responses were measured at 24 and 60 hours after stimulation of cell cultures by LPS.

The LRP/α2M receptor. The LRP/α2M receptor is known. In overview, following modification by lipoprotein lipase and the association of apolipoproteins, very large density lipoproteins (VLDL) and chylomicron become remnants, and are cleared hepatically by a receptor-mediated mechanism. Although recognized as distinct from the low density lipoprotein (LDL) receptor, the remnant receptor also has a high affinity for apolipoprotein E, and recognizes the remnant particles via incorporated apoE moieties. In 1988, this remnant receptor was cloned, and dubbed the LDL receptor-related related protein, or "LRP". The LRP is a large receptor, with a primary sequence of 4525 amino acids, and bears many structural similarities to other members of the LDL receptor family. Like the LDL receptor, the extracellular domain of LRP includes a cysteine-enriched ligand binding domain and EGF precursor homology domain which are believed to play a role in the acid-dependent dissociation of ligand from the receptor. Unlike the LDL receptor, however, the O-lined sugar domain is not present in the extracellular portion adjacent to the membrane. As with all of the members of the LDL receptor family, LRP is a transmembrane protein, and is anchored by a single transmembrane segment. The cytoplasmic tail of the protein is 100 amino acids, approximately twice as long as the LDL receptor, and contains the NPxY motif, which is believed to be necessary for targeted coated-pit mediated endocytosis (See, e.g., Krieger M. Herz J. Structures and functions of multiligand lipoprotein receptors: macrophage scavenger receptors and LDL receptor-related protein (LRP). *Annual Review of Biochemistry*. 63:601-37, 1994. UI: 95069975; Misra UK. Chu CT. Gawdi G. Pizzo SV. The relationship between low density lipoprotein-related protein/alpha 2-macroglobulin (alpha 2M) receptors and the newly described alpha 2M signaling receptor. *Journal of Biological Chemistry*. 269(28):18303-6, 1994).

The ApoE genotype in humans has been correlated with outcome in a variety of acute neurological conditions including cerebral hemorrhage, closed head injury, stroke and cognitive deterioration after cardiopulmonary bypass. See, e.g., Seliger et al., *Neurology* (Abstract) page A213 (1997); Alberts et al., *Stroke* 27:183 (abstract)(1996); Connolly et al., *Stroke* 27:174 (abstract) (1996); Sorbi et al., *Neurology* 46:A307 (abstract) (1996); Newman et al., *Ann. Thorac. Surg.* 59:1326 (1995). ApoE is the primarily apolipoprotein produced in the central nervous system (CNS) and is upregulated after injury. Laskowitz et al., *J. Neuroimmunol.* 76:70 (1997).

ApoE has been demonstrated to have immunomodulatory effects in vitro, including suppression of lymphocyte proliferation and immunoglobulin synthesis after mitogenic challenge. Avila et al., *J. Biol. Chem.* 257:5900 (1982); Edgington and Curtiss, *Cancer Res.* 41:3786 (1981). ApoE is secreted in large quantities by macrophage after peripheral nerve injury, and by astrocytes and oligodendrocytes after CNS injury. Stoll et al., *Glia* 2:170 (1989); Stoll and Mueller, *Neurosci. Lett.* 72:233 (1986).

Apolipoprotein E binds to the low-density lipoprotein (LDL) receptor, as well as to the LDL receptor-related protein (LRP). The region of ApoE that is involved in receptor interaction is in the vicinity of amino acid residues 135-160, and is rich in basic amino acids including arginine and lysine. This interaction of apolipoprotein E and the LDL receptor is important in lipoprotein metabolism. In studies of the LDL receptor-binding activity of apolipoprotein E, it is typically complexed with phospholipid. The protein has been described as essentially inactive in the lipid-free state. Innerarity et al., *J. Biol. Chem.* 254:41864190 (1979).

Various amino acid substitutions in the receptor binding region of ApoE have been studied for their effects on ApoE-LDL receptor binding. Substitution of either arginine or lysine at residues 136, 142, 145 and 146 with neutral residues decreased normal apoE3 binding activity. Weisgraber, *Advances in Protein Chemistry* 45:249 (1994); Lalazar et al., *J. Biol. Chem.* 263:3542 (1988). No single substitution of a basic residue within the receptor-binding region of ApoE3 completely disrupts LDL receptor binding, suggesting that no one residue is critical for this interaction. It has been postulated that regions of ApoE outside the LDL binding region are necessary to maintain the receptor-binding region in an active binding conformation. Weisgraber, *Advances in Protein Chemistry* 45:249 (1994). Dyer et al., *J. Biol. Chem.* 266:15009 (1991), studied lipid-free synthetic peptide fragments comprising residues 141-155 of ApoE, and a dimeric peptide of this sequence. No binding activity was observed with the monomer of this peptide; low levels of binding were observed with the dimer (~1% of LDL activity).

Several receptors that bind ApoE with high affinity have been identified, including the scavenger receptor, VLDL receptor, LDL receptor, and LRP receptors. These three receptors have areas of high sequence similarity. The scavenger receptor is known to be present on microglia, and preferentially binds acytylated and oxidized LDL. The scavenger receptor may be particularly relevant under inflammatory (oxidizing) conditions. Scavenger receptors are also known to be upregulated in microglia after injury. LRP receptors are known to be present on macrophages.

The microglia is the primary immunocompetent cell in the central nervous system. Acute CNS insult, as well as chronic conditions such as HW encephalopathy, epilepsy, and Alzheimer's disease (AD) are associated with microglial activation. McGeer et al., *Glia* 7:88 (1993); Rothwell and Relton, *Cerebrovasc. Brain Metab. Rev.* 5:178 (1993); Giulian et al., *J. Neuroscience*, 16:3139 (1996); Sheng et al., *J. Neurochem* 63:1872 (1994). Microglial activation results in the production of nitric oxide (NO) and other free radical species, and the release of proteases, inflammatory cytokines (including IL-1 β, IL-6 and TNFα), and a neurotoxin that works through the NMDA receptor. Giulian et al., *J. Neuroscience*, 16:3139 (1996). Microglial activation can be assessed by measuring the production of nitrite, a stable product of nitric oxide formation. See, e.g, Barger and Harmon, *Nature* 388:878 (1997).

The present inventors determined that apoE modulates the activation of glia in the CNS, and further identified a peptide that suppresses the activation of microglia. While not wishing to be bound to a single theory, the present inventors hypothesized that ApoE binding to a microglial receptor affects the phenotype of the microglia, decreasing the responsiveness of the microglia to various activators, and therefore decreasing the release of inflammatory compounds from the microglia that would otherwise occur in the presence of such activators. The ApoE may be binding to the same receptor as is bound by the activating compounds, or may be binding to a receptor independent from that bound by activators. In lymphocytes, ApoE has been shown to block activation by a variety of compounds, including LPS, the lectin PHA, and anti-CD3 antibody; these activators are known to bind to distinct receptors on lymphocytes. The methods and compounds of the present invention are designed to prevent or suppress the receptor-mediated activation of microglia, and thus prevent or reduce the deleterious neurological effects associated with activated microglia. Peptides and other therapeutic molecules according to the present invention are able to bind to receptors on glia, and decrease the responsiveness of the cell to various activators. In this manner, methods and compounds according to the present invention may be used to treat, ameliorate, or prevent certain signs, symptoms, and/or deleterious neurological effects of acute and/or chronic CNS injury. The effect of the present methods and compounds may be assessed at the cellular or tissue level (e.g., histologically or morphometrically), or by assessing a subject's neurological status. Methods of assessing a subject's neurological status are known in the art.

Laskowitz et al., *J. Neuroimmunology* 76:70 (June 1997) described experiments in which mixed neuronal-glial cell cultures from apoE-deficient mice were stimulated with lipopolysaccharide (LPS). It was found that preincubation of the cell cultures with apoE blocked glial secretion of TNFα in a dose-dependent manner. Laskowitz et al., *J. Cerebral Blood Flow and Metabolism*, 17:753-758 (July 1997) compared the neurologic and histologic outcome of ApoE-deficient mice subjected to occlusion of the cerebral artery for either 60 or 90 minutes, with a recovery period of 24 hours. When subjected to 60 minutes of occlusion, ApoE-deficient mice were reported to have larger infarcts and more severe hemiparesis than wild-type mice. In mice subjected to 90 minutes of occlusion, mortality was 40% in ApoE-deficient mice compared to 0% in wild-type mice.

Barger S W and Harmon A D, *Nature* 388:878 (August 1997) reported that treatment of microglia with a secreted derivative of beta-amyloid precursor protein (sAPP-alpha) activated microglia, induced inflammatory reactions in microglia, and enhanced the production of neurotoxins by microglia. The ability of sAPP-alpha to activate microglia was blocked by prior incubation of the sAPP-alpha protein with apolipoprotein E3 but not apolipoprotein E4.

Suitable subjects for carrying out the methods of the present invention include male and female mammalian subjects, including humans, non-human primates, and non-primate mammals. Subjects include veterinary (companion animal) subjects, as well as livestock and exotic species.

The present methods and compounds are useful in preventing, treating, or ameliorating neurological signs and symptoms associated with acute CNS injury; as used herein, acute CNS injury includes but is not limited to stroke (caused by thrombosis, embolism or vasoconstriction), closed head injury, global cerebral ischemia (e.g., ischemia due to systemic hypotension of any cause, including cardiac infarction, cardiac arrhythmia, hemorrhagic shock, and post coronary artery bypass graft brain injury) and intracranial hemorrhage. Further, the present methods and compounds are useful in preventing, treating, or ameliorating neurological signs and symptoms associated with chronic neurological disease, including but not limited to Alzheimer's disease (AD) and HIV-associated encephalopathy. The present methods and compounds are also useful in preventing, treating, or ameliorating the neurological signs and symptoms associated with inflammatory conditions affecting the nervous system including the CNS, including but not limited to multiple sclerosis, vasculitis, acute disseminated encephalomyelitis, and Guillain-Barre syndrome.

Stated in a different way, the present methods and compounds are useful in preventing, suppressing or reducing the activation of glia in the CNS that occurs as a part of acute or chronic CNS disease. The suppression or reduction of glial activation can be assessed by various methods as would be apparent to those in the art; one such method is to measure the production or presence of compounds that are known to be produced by activated glia, and compare such measurements to levels of the same compounds in control situations. Alternatively, the effects of the present methods and compounds in suppressing, reducing or preventing microglial activation may be assessed by comparing the signs and/or symptoms of CNS disease in treated and control subjects, where such signs and/or symptoms are associated with or secondary to activation of microglia.

Ischemic damage to the central nervous system may result from either global or focal ischemic conditions. Global ischemia occurs where blood flow to the entire brain ceases for a period of time, such as during cardiac arrest. Focal ischemia occurs when a portion of the brain is deprived of normal blood flow, such as during thromboembolytic occlusion of a cerebral vessel, traumatic head injury, edema and brain tumors. Much of the CNS damage due to cerebral ischemia occurs during the hours or even days following the ischemic condition, and is secondary to the release of cytotoxic products by damaged tissue.

In Alzheimer's disease, studies indicate that anti-inflammatory drugs may delay the onset or progression of the disease. Breitner et al., *Neurobiol. Aging* 16:523 (1995); Rogers et al., *Neurology* 43:1609 (1993). Microglia express markers of activation in AD, suggesting that crucial inflammatory events in AD involve microglia. Such activated microglia cluster near amyloid plaques. Griffin et al., *J. Neuropath. Exp. Neurol.* 54:276 (1995). Microglia are also activated in epilepsy (see Sheng et al., *J. Neurochem* 63:1872 (1994).

In subjects with head injuries, AD-like changes are synergistic with ApoE genotype. The ApoE4 allele has been associated with the extent of amyloid β-protein deposition following head injury. Mayeux et al., *Neurology* 45:555 (1995); Nicoll et al., *Nat. Med.* 1:135 (1995).

As used herein, the terms "combating", "treating" and "ameliorating" are not necessarily meant to indicate a reversal or cessation of the disease process underlying the CNS condition afflicting the subject being treated. Such terms indicate that the deleterious signs and/or symptoms associated with the condition being treated are lessened or reduced, or the rate of progression is reduced, compared to that which would occur in the absence of treatment. A change in a disease sign or symptom may be assessed at the level of the subject (e.g., the function or condition of the subject is assessed), or at a tissue or cellular level (e.g., the production of markers of glial activation is lessened or reduced). Where the methods of the present invention are used to treat chronic CNS conditions (such as Alzheimer's disease), the methods may slow or delay the onset of symptoms such as dementia, while not necessarily affecting or reversing the underlying disease process.

Active Compounds. Active compounds that may be used to carry out the present invention include ligands or agonists that specifically and/or selectively bind to the LRP/α2M receptor. Examples of such compounds include, but are not limited to, 1) alpha 2 macroglobulin; 2) pseudomonas exotoxin; 3) lipoprotein lipase; 4) apolipoprotein E; 5) oxidized and/or acetylated LDL; 6) receptor associated protein (RAP); 7) remnant particles; 8) low density lipoprotein (LDL); 9) high denity lipoprotein (HDL); 10) lactoferrin; 11) tissue plasminogen activator (tPA); 12) urine plasminogen activator (uPA); etc.

Amino acid residues 100-200 of each isoform of the ApoE molecule comprise the ApoE receptor binding region. More specifically, the receptor binding region of ApoE is within amino acid residues 130-160 of each isoform of the ApoE molecule (SEQ ID NO:4 and SEQ ID NO:5), and more specifically is within amino acid residues 140-155 (HLRKLR KRLLRDADDL) (SEQ ID NO:1). See, e.g., Weisgraber, Apolipoprotein E: Structure-Function Relationships, *Advances in Protein Chemistry* 45:249 (1994). The amino acid interchanges that define the E2, E3 and E4 isoforms are not found within the region of amino acid residues 140-155, but do influence the overall structure of the apolipoprotein molecule. ApoE2 and ApoE3 molecules form covalently bound homodimers; ApoE4 molecules do not.

As used herein, the term homodimer refers to a molecule composed of two molecules of the same chemical composition; the term heterodimer refers to a molecule composed of two molecules of differing chemical composition.

The present inventors utilized a 9-mer monomer having an amino acid sequence LRKLRKRLL (SEQ ID NO:2). This 9 amino acid sequence is found within the larger ApoE receptor binding sequence region identified above, and is found at amino acid positions 141-149 of ApoE. The present inventors constructed a dimer of SEQ ID NO:2, i.e., a peptide having an amino acid sequence of LRKLRKRLL LRKLRKRLL (SEQ ID NO:3). Peptides of SEQ ID NO:3 suppressed microglial activation in a dose-dependent fashion. Use of the monomer (monomer peptides of SEQ ID NO:2) did not suppress microglial activation. (See FIG. 2).

The present inventors further utilized a 20-mer monomer having an amino acid sequence TEELRVRLAS HLRKLRKRLL (SEQ ID NO:6). This 20 amino acid sequence is found at amino acid positions 130-149 of ApoE, and comprises the 9-mer SEQ ID NO:2. Peptides of SEQ ID NO:6 suppressed microglial activation in a dose-dependent fashion (see FIGS. 4-7).

Clay et al., *Biochemistry* 34:11142 (1995) reported that dimeric peptides of amino acids 141-155 or 141-149 were both cytostatic and cytotoxic to T lymphocytes in culture. Cardin et al. *Biochem Biophys Res. Commun.* 154:741 (1988) reported that a peptide of apoE 141-155 inhibited the proliferation of lymphocytes. A peptide consisting of a tandem repeat of amino acids 141-155, as well as longer monomeric peptides comprising the 141-155 region, was found to cause extensive and specific degeneration of neurites from embryonic chicks in vitro. Crutcher et al., *Exp. Neurol*. 130:120 (1994). These authors suggested that peptide sequences associated with apoE might contribute directly to neurodegenerative processes.

Peptides of the present invention may be produced by standard techniques as are known in the art.

Active compounds (or "active agents") useful in the methods of the present invention include those that compete with a peptide of SEQ ID NO:3, and/or a peptide of SEQ ID NO:6 in binding to microglial receptors to thereby prevent or suppress activation of the microglia by molecules that would otherwise activate microglia.

Peptides useful in the present methods include those comprising the ApoE LDL receptor binding sequence (including multiple repeats thereof, including but not limited to dimers and trimers); and conjugates of two or more peptides, each of which comprises a peptide as described herein or a peptide comprising the LDL receptor binding sequence. One ApoE receptor binding sequence is provided in SEQ ID NO:1. A preferred peptide comprises or consists of multiple repeats of SEQ ID NO:2, preferably dimers thereof. Thus, a preferred peptide useful in the present methods is SEQ ID NO:3 (a tandem repeat of LRKLRKRLL), or peptides comprising SEQ ID NO:3. Further preferred peptides comprise or consist of SEQ ID NO:4, SEQ ID NO:5, or SEQ ID NO:6.

The ability of a linear tandem repeat of amino acids 141-155 (the 141-155 dimer) to bind the LDL receptor was studied by Dyer et al., *J. Lipid Research* 36:80 (1995). A series of modified peptides was constructed and assessed for LDL binding ability. These authors report that deletion of the charged amino terminal residues (including arg142 and lys43) in 145-155 or 144-150 dimers abolished the LDL receptor activities of the peptides. These authors conclude that LDL-receptor binding activity of the 141-155 dimer is dependent on at least two clusters of basic amino acids present on the hydrophilic face of the amphipathic alpha-helix of the 141-155, 141-150, 141-155 (1lys143-->ala) and 141-155 (arg150-->ala) dimer peptides. Dyer et al., *J. Biol. Chem*. 266:15009 (1991) reported that a self-conjugate of peptide 141-155, and a peptide consisting of a tandem repeat of 141-155, were able to inhibit both lymphocyte proliferation and ovarian androgen production. Dyer et al., *J. Biol. Chem*. 266:22803 (1991) investigated the LDL binding ability of a dimeric 141-155 tandem peptide, and a trimeric 141-155 peptide. Binding was decreased with amino acid substitutions of Lys-143--->Ala, Leul144--->Pro, and Argl50--->Ala.

Lalazar et al., *J. Biol. Chem*. 263:3542 (1988) investigated variants of ApoE for binding to the LDL receptor. When neutral amino acids were substituted for basic residues at positions 136, 140, 143, and 150, binding activity was reduced. Where proline was substituted for leucinel 144 or alanine 152, binding was reduced. However, slightly enhanced receptor binding was displayed by a variant in which arginine was substituted for serine139 and alanine was substituted for leucine 149.

Compounds that are useful in the present method include those which act as antagonists for the microglial receptor bound by peptides of SEQ ID NO:3 and/or SEQ ID NO:6. Antibodies that selectively target and bind to this receptor can also be used as antagonists of microglial activation according to the present invention. Such antibodies selectively or specifically bind to the receptor bound by peptides of SEQ ID NO:3 and/or peptides of SEQ ID NO:6.

Peptides of SEQ ID NO:3, SEQ ID NO:6, or conformational analogues thereof, are an aspect of the present invention. Such compounds are peptides or peptidomimetics having a core sequence of amino acids with a conformation in aqueous solution that interacts with receptor molecules on glial cells to block the activation of glial cells that would otherwise occur in conjunction with acute or chronic CNS injury, or exposure to known activators of microglia such as LPS. Stated another way, such compounds are characterized by the ability to compete with peptides of SEQ ID NO:3 and/or peptides of SEQ ID NO:6 for binding to microglia, and by their ability to suppress microglial activation by known activators such as LPS.

Another variation of the therapeutic peptides of the present invention is the linking of from one to five amino acids or analogues to the N-terminal or C-terminal amino acid of the therapeutic peptide. Analogs of the peptides of the present invention may also be prepared by adding from one to five additional amino acids to the N-terminal, C-terminal, or both N- and C-terminals, of an active peptide, where such amino acid additions do not adversely affect the ability of the peptide to bind to microglia at the site bound by a peptide of SEQ ID NO:3 and/or SEQ ID NO:6.

Changes in the amino acid sequence of peptides can be guided by known similarities among amino acids and other molecules or substituents in physical features such as charge density, hydrophobicity, hydrophilicity, size and configuration, etc. For example, the amino acid Thr may be replaced by Ser and vice versa, and Leu may be replaced by Ile and vice versa. Further, the selection of analogs may be made by mass screening techniques known to those skilled in the art (e.g., screening for compounds which bind to microglia at the receptor bound by a peptide of SEQ ID NO:3 and/or SEQ ID NO:6). A preferred exchange is to replace Ser with Arg, to increase the arginine content of the peptide; examples include peptides of or comprising SEQ ID NO:7, SEQ ID NO:8 or SEQ ID NO:9. A further preferred exchange is to substitute alanine for leucine 149.

Peptides of the present invention may also be characterized as short peptides of from about 20 amino acids, 22 amino acids, 24 amino acids, 26 amino acids, 28 amino acids, 30 amino acids, 35 amino acids, or 40 amino acids, up to about 22 amino acids, 24 amino acids, 26 amino acids, 28 amino acids, 30 amino acids, 35 amino acids, 40 amino acids, 45 amino acids, 50amino acids or more, where the peptides comprise the 18-amino acid sequence LRKL-RKRLL LRKLRKRLL (SEQ ID NO:3), or variants thereof that retain the receptor binding ability of peptides of SEQ ID NO:3. A preferred peptide useful in the present invention is one consisting of or comprising SEQ ID NO:3. Where longer peptides are employed, those incorporating amino acid sequences derived from the ApoE sequence immediately surrounding amino acid residues 141-149 are preferred. Where peptides longer than 18 amino acids are employed, it is contemplated that they may include virtually any other amino acid sequences so long as the resultant peptide maintains its ability to bind to microglial and suppress microglia activation in acute and chronic CNS inflammation. The present invention includes those variations of the ApoE sequence at 141-149 which are known to retain the ability LDL receptor-binding ability. Synthetic peptides may further be employed, for example, using one or more D-amino acids in place of L-amino acids, or by adding groups to the N- or C-termini, such as by acylation or amination.

Peptides of the present invention may also be characterized as short peptides of from about 10 amino acids, 12 amino acids, 14 amino acids, 15 amino acids, 18 amino acids, 20 amino acids, 22 amino acids, 24 amino acids, 26 amino acids, 28 amino acids, 30 amino acids, 35 amino acids, or 40 amino acids, up to about 15 amion acids, 22 amino acids, 24 amino acids, 26 amino acids, 28 amino acids, 30 amino acids, 35 amino acids, 40 amino acids, 45 amino acids, 50 amino acids or more, where the peptides comprise the 9-amino acid sequence LRKLRKRLL (SEQ ID NO:2), or variants thereof that retain the receptor binding ability of peptides of SEQ ID NO:3 and/or SEQ ID NO:6. A preferred peptide useful in the present invention is one consisting of or comprising the apoE receptor binding region; a particularly preferred peptide consists of or comprises SEQ ID NO:6. Where longer peptides are employed, those incorporating amino acid sequences derived from within the apoE receptor binding regtion, or the ApoE sequence immediately surrounding the apoE receptor binding region, are preferred, although it is contemplated that these peptides may include virtually any other amino acid sequences so long as the resultant peptide maintains its ability to bind to microglia and suppress microglia activation in acute and chronic CNS inflammation. The present invention includes those variations of the ApoE sequence at 141-149 which are known to retain the ability LDL receptor-binding ability. Synthetic peptides may further be employed, for example, using one or more D-amino acids in place of L-amino acids, or by adding groups to the N- or C-termini, such as by acylation or amination.

The peptides of the present invention include not only natural amino acid sequences, but also peptides which are analogs, chemical derivatives, or salts thereof. The term "analog" or "conservative variation" refers to any polypeptide having a substantially identical amino acid sequence to the therapeutic peptides identified herein, and in which one or more amino acids have been substituted with chemically similar amino acids. For example, a polar amino acid such as glycine or serine may be substituted for another polar amino acid; a basic amino acid may be substituted for another basic amino acid, or an acidic amino acid may be substituted for another acidic amino acid; or a non-polar amino acid may be substituted for another non-polar amino acid. There term "analog" or "conservative variation" as used herein also refers to a peptide which has had one or more amino acids deleted or added to a polypeptide of the present invention, but which retains a substantial sequence similarity (at least about 85% sequence similarity, and preferably at least 90%, 92%, 94%, 95%, 96%, 98% or even 99% sequence similarity), where the peptide retains the ability to suppress microglial activation as described herein.

The amino acids constituting peptides of the present invention may be of either the L-configuration or the D-configuration. Therapeutic peptides of the present invention may be in free form or the form of a salt, where the salt is pharmaceutically acceptable.

As used herein, the term "administering to the brain of a subject" refers to the use of routes of administration, as are known in the art, that provide the compound to the central nervous system tissues, and in particular the brain, of a subject being treated.

Preferably, the compounds of the present invention are used in combination with a pharmaceutically acceptable carrier. The present invention thus also provides pharmaceutical compositions suitable for administration to mammalian subjects. Such compositions comprise an effective amount of the compound of the present invention in combination with a pharmaceutically acceptable carrier. The carrier may be a liquid, so that the composition is adapted for parenteral administration, or may be solid, i.e., a tablet or pill formulated for oral administration. Further, the carrier may be in the form of a nebulizable liquid or solid so that the composition is adapted for inhalation. When administered parenterally, the composition should by pyrogen free and in an acceptable parenteral carrier. Active compounds may alternatively be formulated encapsulated in liposomes, using known methods. Additionally, the intranasal administration of peptides to treat CNS conditions is known in the art (see, e.g., U.S. Pat. No. 5,567,682 to Pert, regarding intranasal administration of peptide T to treat AD). (All patents referenced herein are intended to be incorporated by reference herein in their entirety.) Preparation of a compound of the present invention for intranasal administration may be carried out using techniques as are known in the art.

Pharmaceutical preparations of the compounds of the present invention may optionally include a pharmaceutically acceptable diluent or excipient.

An effective amount of the compound of the present invention is that amount that decreases microglial activation compared to that which would occur in the absence of the compound; in other words, an amount that decreases the production of neurotoxic compounds by the microglia, compared to that which would occur in the absence of the compound. The effective amount (and the manner of administration) will be determined on an individual basis and will be based on the specific therapeutic molecule being used and a consideration of the subject (size, age, general health), the condition being treated (AD, acute head injury, cerebral inflammation, etc.), the severity of the symptoms to be treated, the result sought, the specific carrier or pharmaceutical formulation being used, the route of administration, and other factors as would be apparent to those skilled in the art. The effective amount can be determined by one of ordinary skill in the art using techniques as are known in the art. Therapeutically effective amounts of the compounds described herein may be determined using in vitro tests, animal models or other dose-response studies, as are known in the art.

The compounds of the present invention may be administered acutely (i.e., during the onset or shortly after events leading to cerebral inflammation or ischemia), or may be administered prophylactically (e.g., before scheduled surgery, or before the appearance of neurologic signs or symptoms), or administered during the course of a degenerative disease to reduce or ameliorate the progression of symptoms that would otherwise occur. The timing and interval of administration is varied according to the subject's symptoms, and may be administered at an interval of several hours to several days, over a time course of hours, days, weeks or longer, as would be determined by one skilled in the art.

The typical daily regime may be from about .01 µg/kg body weight per day, from about 10 µg/kg body weight per day, from about 100 µg/kg body weight per day, from about 1000 µg/kg body weight per day, from about 10,000 µg/kg body weight per day, from about 100,000 µg/kg body weight per day.

The blood-brain barrier presents a barrier to the passive diffusion of substances from the bloodstream into various regions of the CNS. However, active transport of certain agents is known to occur in either direction across the blood-brain barrier. Substances that may have limited access to the brain from the bloodstream can be injected directly into the cerebrospinal fluid. Cerebral ischemia and inflammation are also known to modify the blood-brain barrier and result in increased access to substances in the bloodstream.

Administration of a compound directly to the brain is known in the art. Intrathecal injection administers agents directly to the brain ventricles and the spinal fluid. Surgically-implantable infusion pumps are available to provide sustained administration of agents directly into the spinal fluid. Lumbar puncture with injection of a pharmaceutical compound into the cerebrospinal fluid ("spinal injection") is known in the art, and is suited for administration of the present compounds.

Pharmacologic-based procedures are also known in the art for circumventing the blood brain barrier, including the conversion of hydrophilic compounds into lipid-soluble drugs. The active agent may be encapsulated in a lipid vesicle or liposome.

The intra-arterial infusion of hypertonic substances to transiently open the blood-brain barrier and allow passage of hydrophilic drugs into the brain is also known in the art. U.S. Pat. No. 5,686,416 to Kozarich et al. discloses the co-administration of receptor mediated permeabilizer (RMP) peptides with compounds to be delivered to the interstitial fluid compartment of the brain, to cause an increase in the permeability of the blood-brain barrier and effect increased delivery of the compounds to the brain. Intravenous or intraperitoneal administration may also be used to administer the compounds of the present invention.

One method of transporting an active agent across the blood-brain barrier is to couple or conjugate the active agent to a second molecule (a "carrier"), which is a peptide or non-proteinaceous moiety selected for its ability to penetrate the blood-brain barrier and transport the active agent across the blood-brain barrier. Examples of suitable carriers include pyridinium, fatty acids, inositol, cholesterol, and glucose derivatives. The carrier may be a compound which enters the brain through a specific transport system in brain endothelial cells. Chimeric peptides adapted for delivering neuropharmaceutical agents into the brain by receptor-mediated transcytosis through the blood-brain barrier are disclosed in U.S. Pat. No. 4,902,505 to Pardridge et al. These chimeric peptides comprise a pharmaceutical agent conjugated with a transportable peptide capable of crossing the blood-brain barrier by transcytosis. Specific transportable peptides disclosed by Pardridge et al. include histone, insulin, transferrin, and others. Conjugates of a compound with a carrier molecule, to cross the blood-brain barrier, are also disclosed in U.S. Pat. No. 5,604,198 to Poduslo et al. Specific carrier molecules disclosed include hemoglobin, lysozyme, cytochrome c, ceruloplasmin, calmodulin, ubiquitin and substance P. See also U.S. Pat. No. 5,017,566 to Bodor.

An alternative method of administering peptides of the present invention is carried out by administering to the subject a vector carrying a nucleic acid sequence encoding the peptide, where the vector is capable of entering brain cells so that the peptide is expressed and secreted, and is thus available to microglial cells. Suitable vectors are typically viral vectors, including DNA viruses, RNA viruses, and retroviruses. Techniques for utilizing vector deliver systems and carrying out gene therapy are known in the art. Herpesvirus vectors are a particular type of vector that may be employed in administering compounds of the present invention.

Screening Methods. Also disclosed herein are methods of screening compounds for the ability to prevent or reduce microglial activation under conditions of cerebral ischemia or cerebral inflammation. Such methods comprise contacting an activated microglial cell with a test compound, and detecting whether the test compound binds to microglia at the same receptor at which peptides of SEQ ID NO:3 and/or SEQ ID NO:6 bind. The contacting step may be carried out in vitro, for example in cell culture. A competitive binding assay may be used to detect whether the test compound binds to the same receptor that is bound by peptides of SEQ ID NO:3 and/or SEQ ID NO:6.

An additional method of screening a test compound for the ability to suppress microglial activation comprises incubating an activated microglial cell culture with a test compound, and measuring at least one marker of microglial activation. A decrease in a marker of microglial activation (compared to the level of that marker that would occur in the absence of the test compound) indicates that the test compound is able to suppress, prevent or reduce microglial activation. An exemplary marker of microglial activation is the production of nitric oxide.

A further method of screening a test compound for the ability to suppress microglial activation involves pre-incubating a microglial cell culture with a test compound, then incubating the microglial cell culture with a compound that is known to activate microglia. At least one marker of microglial activation is then measured, and a decrease in the activation marker (compared to that which occurs in the absence of the pre-incubation step) indicates that the test compound is able to affect microglial activation. An exemplary marker of microglial activation is the production of nitric oxide.

Atherosclerosis. It known that the inflammatory process mediates an aspect of the atherosclerotic process. See, e.g., Hansson, *Basic Res. Cardiol.*, 89(1):41 (1994); Berliner et al., *Circulation* 91:2488 (1995); Watanabe et al., *Int. J. Cardiol.* 54:551 (1997). ApoE is known to be secreted by macrophages locally at blood vessel walls (although the amount secreted by macrophages in an individual is trivial compared to the amount of ApoE produced by the liver). In the classic model of atherosclerosis, ApoE functions to remove cholesterol from the blood stream and deliver it to macrophages or to the liver. However, it has become apparent that ApoE secreted by macrophages at the blood vessel wall decreases atherosclerotic plaque formation, independent of any lipid metabolism effects. ApoE-deficient mice are accepted as a model of hypercholesteremia and atherosclerotic disease; providing ApoE-secreting macrophages to such mice dramatically decreases atherosclerotic plaque formation. Linton et al., *Science*, 267:1034 (1995). Conversely, replacing a wild-type mouse's macrophages with ApoE-deficient macrophages accelerates atherosclerotic changes, even though the animal continues to produce ApoE by the liver. Fazio et al., *Proc. Natl. Acad. Sci.* 94:4647 (1997). In atherosclerosis it is hypothesized that ApoE, via a receptor-mediated event, downregulates macrophage activation in the vicinity of blood vessel walls. Such downregulation of macrophage activation interrupts or interfers with the cascade of events associated with atherosclerotic plaque formation, to thereby reduce or slow the formation of atherosclerotic lesions. The cascade of events known to be associated with atherosclerosis includes smooth muscle cell and endothelial cell proliferation, and foam cell formation; evidence exists that ApoE downregulates each of these processes. ApoE thus affects the presence and progression of atherosclerosis in vivo, independent of its effects on lipids. The progression of atherosclerosis may be assessed by measuring the amount or size of atherosclerotic plaques, or the percentage of the blood vessel blocked by an atherosclerotic lesion, or the rate of growth of such plaques.

The present inventors have for the first time demonstrated that ApoE transduces a calcium-mediated signal ($Ca^{2+}$/inositol triphosphate signal transduction) in macrophage, indicating that ApoE modifies macrophage function by downregulating macrophage activation and, therefore, subsequent inflammation. Peptides, compounds, methods and pharmaceutical formulations as described herein in relation to microglia and CNS disease are accordingly useful in methods of suppressing the activation of macrophages to suppress, prevent, or slow atherosclerosis. Atherosclerosis refers to the thickening of the arterial intima and accumulation of lipid in artherosclerotic plaques. Administration of compounds of the present invention to treat or prevent atherosclerosis may be by any means discussed herein as well as other suitable methods that are known in the art. When using the present compounds to prevent, slow or treat atherosclerotic changes, it is apparent that they need not be formulated to pass through the blood brain barrier. Conditions that may be treated by the present method include atherosclerosis of the coronary arteries; arteries supplying the Central Nervous system, such as carotid arteries; arteries of the peripheral circulation or the splanchnic circulation; and renal artery disease. Administration, such as parenteral administration, may be site-specific or into the general blood stream.

The examples which follow are set forth to illustrate the present invention, and are not to be construed as limiting thereof.

EXAMPLE 1

Microglial Nitric Oxide Production Materials and Methods

This study examined the role of endogenous apoE in modulating microglial nitric oxide (NO) production, as measured by nitrite accumulation following lipopolysaccharide (LPS) stimulation of microglia.

Culture preparation and characterization:

Mixed glial cell cultures were prepared from: (a) wildtype (C57/B16; Jackson Laboratories) mouse pups; (b) ApoE deficient mutant mouse pups (ApoE-deficient mice), and (c) transgenic mouse pups expressing human ApoE3 but not murine ApoE (ApoE3 mice). See Xu et al., *Neurobiol. Dis.* 3:229 (1996) regarding the creation and characterization of the transgenic mice. Mixed glial cell cultures were prepared as has been described. See McMillian et al., *Neurochem.* 58:1308 (1992); Laskowitz et al., *J. Neuroimmunol.* 76:70 (1997). Briefly, brains were removed from 2-4 day old pups, cleaned of membranes and blood vessels, mechanically dispersed in $Ca^{+2}$-free media, and collected by centrifugation. Cells were then plated in DMEM/F12 (containing 10% fetal calf serum, 1% penicillin/streptomycin, Gibco #15070), one brain per 25 cm flask. Mixed neuronal/glial preparations were grown in humidified incubators until confluent (3-5 weeks).

The percentage of microglia, astrocytes and neurons were quantified to demonstrate that cultures prepared from ApoE-deficient and ApoE3 mice had comparable glial populations. Immunostaining was performed using antibodies to glial fibrillary acidic protein (GFAP; SIGMA®; 1:500 dilution) and tau protein (SIGMA®; 1:500 dilution) to estimate numbers of astrocytes and neurons, and peroxidase-coupled Bandeiraea simplifolica B4 isolectin and naphthyl acetate esterase staining was used to detect microglia. Laskowitz et al., *J. Neuroimmunol.* 76:70 (1997). A mixed neuronal-glial culture system was used, as this most closely approximates the normal CNS milieu, and allows glia-glia interactions, which play a role in the inflammatory cascade.

Comparable glial populations were confirmed using semiquantitative Western blot analysis performed for astrocytes (αGFAP; SIGMA®), neurons ((αtau; SIGMA®) and microglia (Bandeiraea simplifolica B4 isolectin; SIGMA®). Cellular protein was harvested at the end of experiments and 50 μg protein from each sample was separated by polyacrilamide gel electrophoresis and the protein was transferred to nylon membranes. Non-specific binding of antisera and lectin was blocked by preincubation of the membrane in 4% dried milk, 0.1% Triton X-100. Membranes were incubated overnight with antibodies or 1 μg/ml B4 isolectin. After extensive washing in phosphate-buffered saline, bound antibody or lectin was visualized by an ABC kit (Vector, Burlingame, CA), using diaminobenzidine as substrate.

Culture Stimulation:

Cultures were plated in serum-free media after washing cells once with this media, and stimulated with LPS 100 ng/ml (SIGMA®). Aliquots were taken at 24 and 60 hours for nitrite assay.

Nitrite Quantification:

The production of NO was assessed by measuring the accumulation of nitrite, which was quantified using a colorimetric reaction with Griess reagent (0.1% N-1-naphthyl-ethylenediamine dihydrochloride, 1% sulfanilamide, and 2.5% $H_3PO_4$). Absorbance was measured at 570 nm by spectrophotometry. The sensitivity of this assay is approximately 0.5 μm.

Statistical Analysis:

Data were compared by ANOVA and the Fischer LSD multiple range test; $p<0.05$ was considered significant.

EXAMPLE 2

Microglial Nitric Oxide Production: Results

Culture Characterization:

No significant differences were found in glial populations among the cultures prepared from ApoE-deficient, ApoE3, and wild-type mice. Cultures comprised approximately 70% astrocytes, 15% microglia and 15% neurons. Comparisons of cellular preparations from wildtype mice, ApoE-deficient mice and ApoE3 mice showed no differences in glial populations. In particular, levels of microglia (the primary effector cells for NO production) were comparable in all three culture preparations, as detected by lectin binding (data not shown).

ApoE-deficient mouse cultures showed robust nitrite responses during the first 24 hours of exposure to LPS. This enhanced response was 6-fold greater than that observed with microglia from control animals ($p=0.0001$; FIG. 1). Cultures from transgenic mice in which murine apoE is replaced with human ApoE3 show weak responses to LPS that were not significantly different than responses of wildtype animals ($p=0.64$ and $p=0.2$ at 24 and 60 hours, respectively). By 60 hours, increased nitrite accumulation was observed in response to LPS in wildtype and ApoE3 transgenic mouse preparations, although there was still a significantly greater amount of nitrite in the apoE deficient culture as compared to controls ($p=0.04\%$; FIG. 1)

The above studies show that ApoE deficient mixed neuronal-glial cultures respond differently to LPS stimulation than glial cultures prepared from mice expressing native murine ApoE3 or those expressing the human ApoE3 isoform. These results are consistent with ApoE being a biologically relevant mediator of the CNS response to injury. These studies demonstrate that endogenous ApoE modulates glial secretion of LPS-stimulated nitric oxide production, and suggest that one function of endogenous ApoE produced within the brain is to suppress microglial reactivity and thus alter the CNS response to acute and chronic injury.

17

EXAMPLE 3

Suppression of Microglial Activation by Peptides of SEQ ID NO:3

Enriched microglia primary cultures were prepared from the brains of apoE deficient mouse pups as described in Example 1, above. The microglia were stimulated with lipopolysaccharide (100 ng/ml) to activate the microglia as described in Example 1. Activated microglia secrete inflammatory cytokines and nitric oxide; the secretion of nitric oxide was used in the present experiment as a marker of microglial activation. Nitric oxide production was assessed as described in Example 1.

Figure 2:
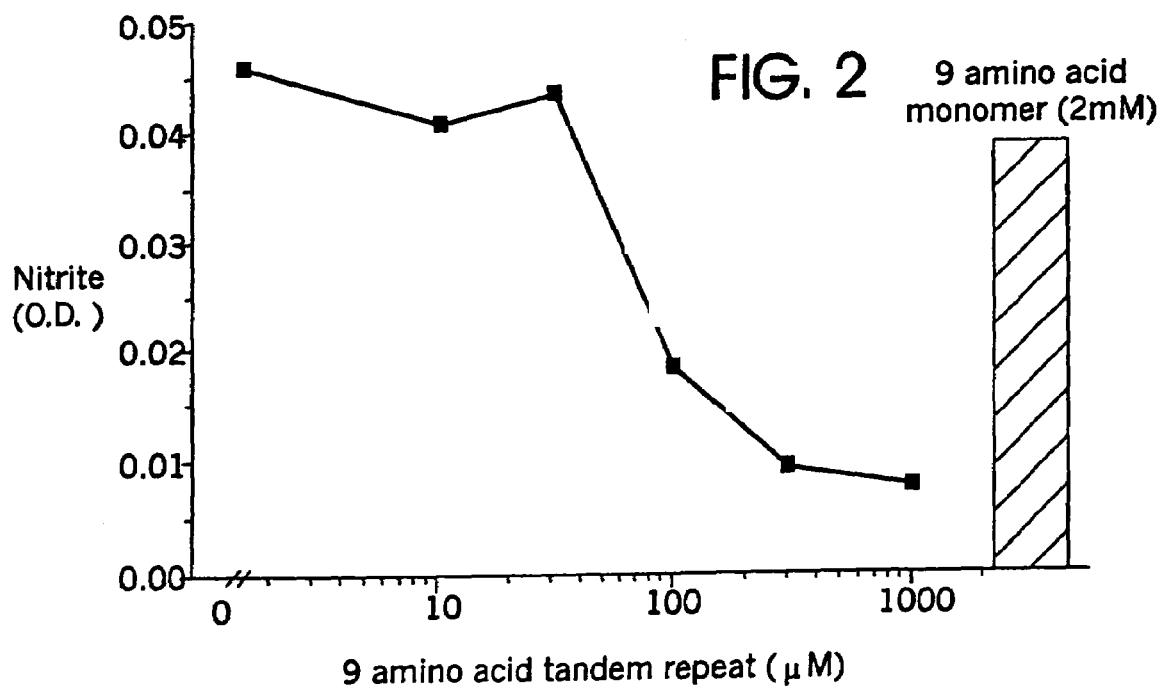
FIG. 2 graphs nitrite production by enriched microglia primary cultures from ApoE-deficient mice after stimulation with LPS and subsequent addition of peptides of SEQ ID NO:3 (tandem repeat peptides). Peptides were added in doses of from 0 μM to 1000 μM, and a dose dependent decrease in nitrite production was observed. As a control, peptides of SEQ ID NO:2 were added to cultures (solid bar); no decrease in nitrite production was observed.

Peptides of SEQ ID NO:3 were added to cultures of activated microglia, in dosages of from 0 µM to 1000 µM. A dose-dependent decrease in nitric oxide secretion was observed after 48 hours (FIG. 2). The administration of a peptide of SEQ ID NO:2 in a dose of 2 mM did not result in any apparent decrease in nitric oxide secretion (FIG. 2). The monomer peptide of SEQ ID NO:2 acted as a control to establish that the observed results are not due to any non-specific peptide effect.

EXAMPLE 4

Effect of ApoE an Macrophage

Intracellular signaling pathways of ApoE were investigated using peritoneal macrophage.

Figure 3A:
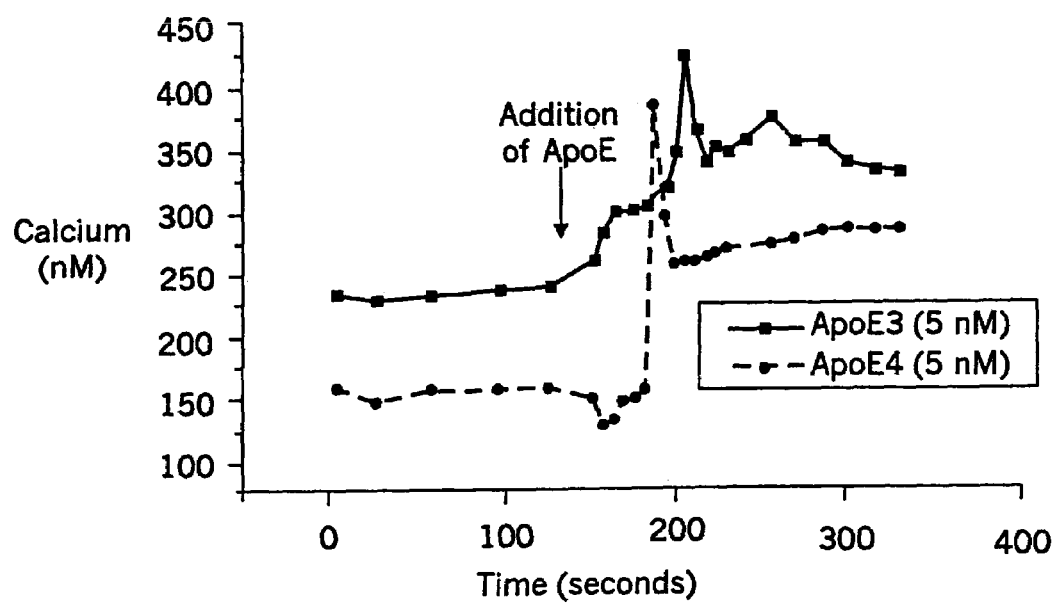
FIG. 3A graphs intracellular calcium content over time in murine peritoneal macrophages, after exposure to either ApoE3 (squares) or ApoE4 (circles).

Thioglycolate-elicited peritoneal macrophage were harvested from 8-week old C57-BL6 mice, and plated at a density of $4 \times 10^5$ cells on glass coverslips, loaded with 2.5 µM Fura-2/AM for thirty minutes, and washed with Hanks buffered solution containing 75 µM calcium. After exposure to 5nM human recombinant apoE3 or E4, intracellular calcium was measured by Zeiss digital microscopy. As shown in FIG. 3A, ApoE caused intracellular mobilization of intracellular calcium in the macrophage. Preincubation with 100 molar excess of Receptor Associated Protein (RAP) did not block this effect; RAP is a physiological antagonist to LRP and blocks the function of LRP.

Macrophage were also plated at a density of $2 \times 10^6$ cells/well, labeled with $^3$H-myoinositol (8 µC/ml) 16 hours at 37 degrees, and exposed to human ApoE3 or ApoE4 (5 nM). Control cells were exposed to vehicle but not ApoE. Results are shown in FIG. 3B; values are expressed as the percent change in inositol trisphosphate in treated cells as compared to control cells.

Figure 3B:
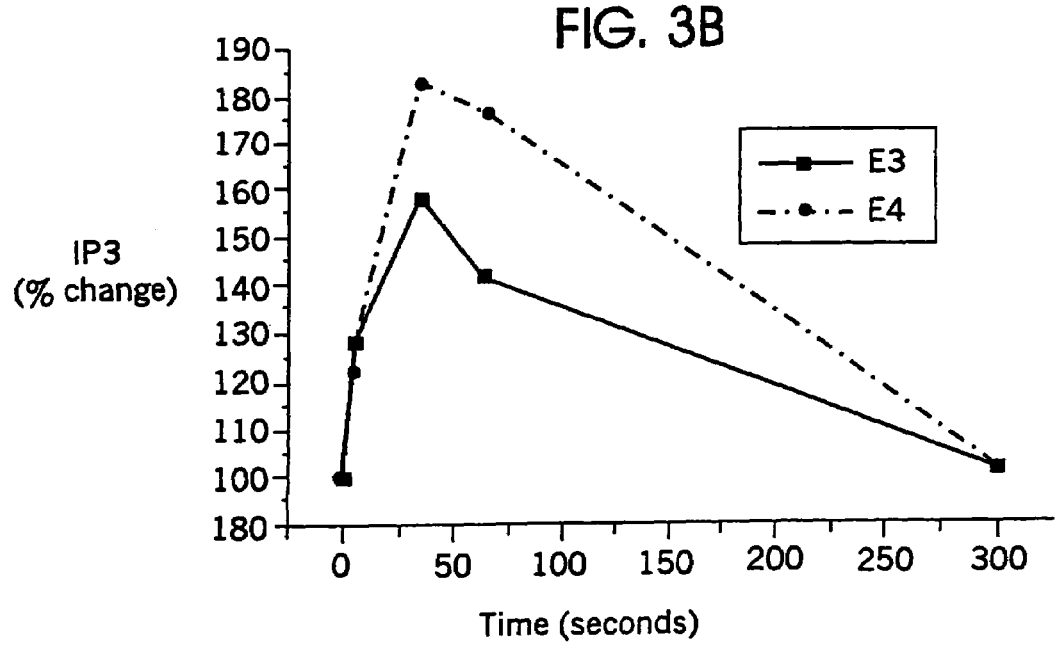
FIG. 3B graphs inositol trisphosphate (IP3) in murine peritoneal macrophages exposed to either ApoE3 (squares) or ApoE4 (circles). The graph shows the percent change in IP3 content in treated cells compared to control cells exposed to vehicle but not ApoE.

Exposure of peritoneal macrophage to ApoE induced a rise in intracellular calcium associated with turnover of inositol tris-phosphate (FIGS. 3A and 3B). The present results indicate that ApoE initiates a signal transduction pathway that affects and modifies macrophage function. The present data suggest that ApoE downregulates macrophage activation and inflammation; macrophage activation and inflammation is known to contribute to the atherosclerotic process.

EXAMPLE 5

Suppression of Microglial Activation Using Peptides of SEQ ID NO:6

A 20-amino acid peptide derived from the receptor binding region of apoE, containing amino acids 130-149 (SEQ ID NO:6) was prepared according to methods known in the art.

18

Primary murine microglial cultures were prepared as described in Example 1, from apoE deficient mouse pups. In some cultures the microglia were activated with lipopolysaccharide (100 ng/ml), as described in Example 1.

Peptides of SEQ ID NO:6 were added to cultures of activated and non-activated microglia, in dosages of 0 µM (control), 10 µM, 100 µM and 1000 µM (FIG. 4). Each dosage level of peptide was tested alone (squares) and in combination with LPS (100 ng/ml; circles). The production of TNFα was then measured 24 hours after addition of the peptides. A decrease in TNFα production by activated microglia (compared to control culture) was observed with each peptide dose used (FIG. 4, circles). Data in FIG. 4 is presented in at least triplicate at each dose; error bars represent standard error of the mean).

These results indicate that peptides of SEQ ID NO:6 suppress cytokine release from activated glial cells.

EXAMPLE 6

Cytotoxicity of Peptides of SEQ ID NO:6

The toxic effects of peptides of SEQ ID NO:6 was investigated. Cultures of activated (LPS) and non-activated microglia, as described in Example 5, were used. Peptides having SEQ ID NO:6 were added to cell cultures in amounts of 0 µM (control), 10 µM, 100 µM and 1000 µM; each dosage level of peptide was tested alone (squares) and in combination with LPS (100 ng/ml; circles). Cell viability was then measured by optical density 24 hours after addition of the peptides.

As shown in FIG. 5, optical density was approximately the same in cultures receiving 0 µM and 10 µM of peptide, but decreased in cultures receiving 100 µM or 1000 µM. These results, taken with the results of Example 5, indicate that a non-toxic concentration of a peptide of SEQ ID NO:6 is sufficient to suppress glial cytokine release.

EXAMPLE 7

Suppression of Glial Cytokines and Cytotoxicity of Peptides of SEQ ID NO:6

Figure 6:
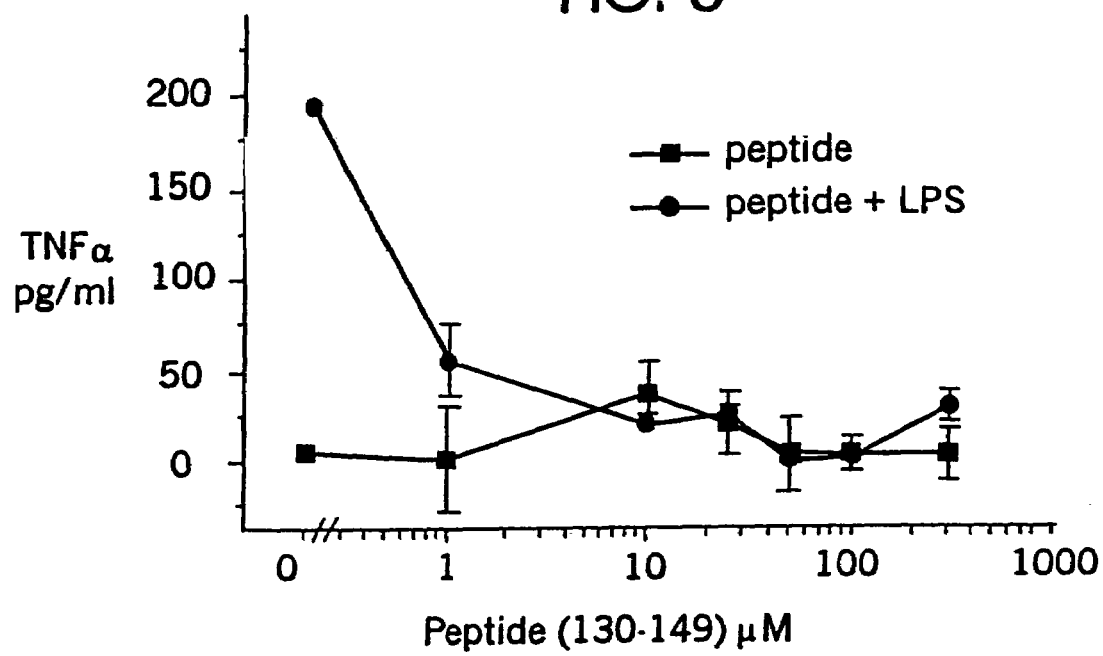
FIG. 6 graphs production of TNFα(picogram/ml) by microglia primary cultures from ApoE-deficient mice after addition of peptides of SEQ ID NO:6 (squares), or addition of peptides of SEQ ID NO:6 and LPS (100 ng/ml) (circles). Peptides were added in doses of 1 μM, 10 μM, 100 μM and 1000 μM.
Figure 7:
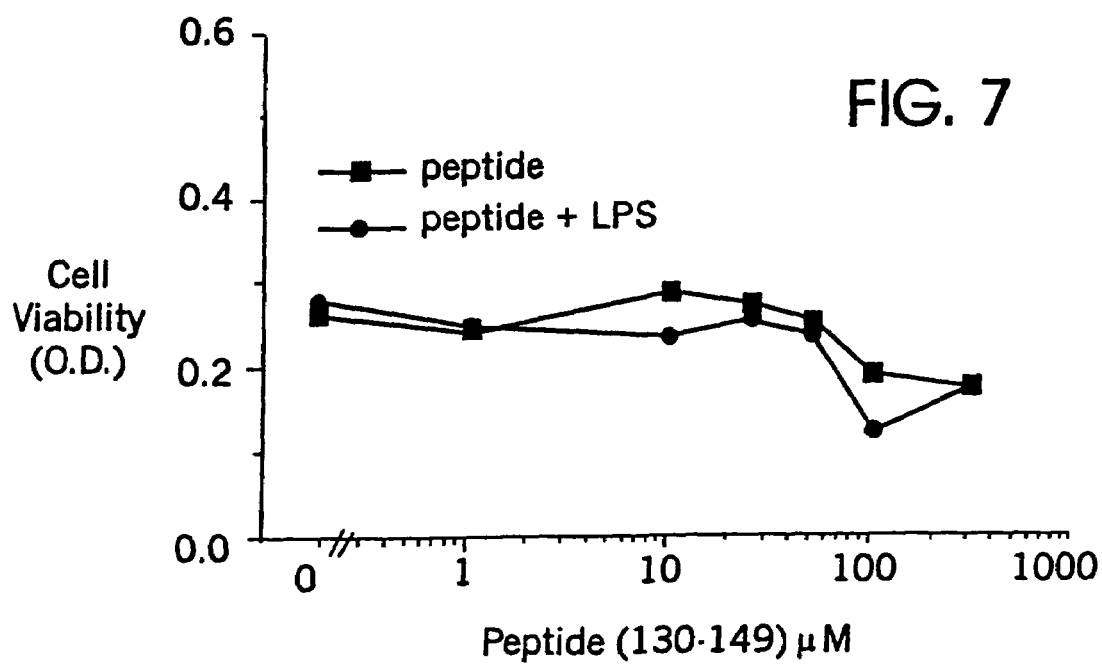
FIG. 7 is a graph of the optical density of cell cultures, as a measure of cell viability. Cultures of microglia from ApoE-deficient mice were exposed to either peptides of SEQ ID NO:6 (squares), or peptides of SEQ ID NO:6 and LPS (100 ng/ml) (circles). Peptides were added in doses of 10 μM, 100 μM and 1000 μM.

The experiments as described in Examples 5 and 6 were repeated using a peptide doses of 0 µM (control), 1 µM, 10 µM, 100 µM and 1000 µM. Each dosage level of peptide was tested alone (squares) and in combination with LPS (100 ng/ml; circles). The production of TNFα was measured 24 hours after administration of the peptides, and results are shown in FIG. 6. The optical density of the cell cultures was also measured (at 24 hours) to assess cell viability; results are shown in FIG. 7.

These results show that microglial cytokine release was suppressed in cell cultures receiving as little as 1 µM of peptide, but cytotoxic effects were seen only in cultures receiving much larger doses of peptide. The results of examples 5-7 indicate that non-toxic concentrations of peptides comprising the receptor binding region of apoE are able to suppress cytokine release from activated microglia.

EXAMPLE 8

In vivo Treatment of Focal Ischemia

A murine model of focal ischemia-reperfusion is used to assess the effects of intrathecal, intravenous or intraperitoneal administration of small therapeutic peptides (fewer than 30 amino acids in length) comprising the apoE LDL receptor region. One such peptide has SEQ ID NO:6.

Wild-type mice are subjected to middle cerebral artery occlusion and reperfusion according to techniques known in the art (see, e.g, Laskowitz et al., *J. Cereb. Blood Flow Metab.* 17:753 (July 1997)). One group of mice (wild-type control) receives no treatment after cerebral artery occlusion; in a similar group (wild-type treatment group) each mouse receives intrathecal, intraperitoneal or intravenous injection of a therapeutic peptide. Therapeutic peptides may be injected in varying doses, using the in vitro data provided above as an initial guide.

Each animal is evaluated neurologically at a predetermined time after reperfusion (e.g., 24 hours after reperfusion) (see, e.g. Laskowitz et al., *J. Cereb. Blood Flow Metab.* 17:753 (July 1997)). After neurological examination each mouse is anesthetized and sacrificed and the brain is sectioned and stained, and infarct volume is measured. Neurological outcome and infarct size is compared between control and treatment groups.

The above experiments may be repeated using apoE deficient mice.

EXAMPLE 9

In vivo Treatment of Global Ischemia

A murine model of global ischemia, adapted from the rat two vessel occlusion model of global ischemia, is used to assess the effects of intrathecal administration of small therapeutic peptides (fewer than 30 amino acids in length) comprising the apoE LDL receptor region. One such peptide has SEQ ID NO:6.

Wild-type mice (21±1 grams) are fasted overnight, anesthetized with halothane or another suitable anesthetic, intubated and mechanically ventilated. The right internal jugular vein and femoral artery are cannulated. Pericranial temperature is held at 37.0° C. The carotid arteries are occluded and mean arterial pressue is reduced to 35 mmHg with 0.3 mg intra-arterial trimethaphan and venous exsanguination. Ten minutes later ischemia is reversed. Control mice receive no additional treatment, test mice receive intrathecal, intravenous or intraperitoneal injection of a therapeutic peptide. Peptides may be injected at varying doses, using the in vitro data provided herein as a guide.

Each animal is evaluated neurologically at a predetermined time (e.g., 1, 3 or 5 days after reperfusion), using known neurological testing procedures (see, e.g., Laskowitz et al., *J. Cereb. Blood Flow Metab.* 17:753 (July 1997)). After neurological evaluation, each animal is anesthetized and sacrificed and the brain injury is assessed using methods known in the art. For example, brains may be perfusion fixed in situ, then sectioned, stained and examined by light microscopy, for example, to determine injury to the CA1 sector of the hippocampus, and viable and non-viable neurons counted and compared.

Neurological outcome and brain injury is compared between control and treatment groups.

EXAMPLE 10

Apolipoprotein E and apoE-Mimetic Peptides Initiate a Calcium-Dependent Signaling Response in Macrophages This example shows that apoE initiates a signaling cascade in murine peritoneal macrophage that is associated with mobilization of intracellular $Ca^{2+}$ stores following increased production of inositol trisphosphate. This cascade was inhibited by pretreatment with receptor-associated protein and $Ni^{2+}$. Signal transduction was mediated by a pertussis toxin-sensitive G protein. These are characteristic properties of signal transduction induced via ligand binding to the lipoprotein receptor-related protein (LRP) receptor. A peptide derived from the receptor binding region of apoE also initiated signal transduction in the same manner as the intact protein. The presence of cross desensitization suggested that the apoE and the apoE-mimetic peptide competed for the same binding site. This was confirmed by our observation that radiolabeled apoE-mimetic peptide competed with the intact protein for receptor binding. These data indicates that ApoE-dependent signal transduction mediates the immunomodulatory properties of this lipoprotein.

A. Materials And Methods

Materials. Brewer's thioglycollate broth was purchased from Difco Laboratories (Baltimore, MD). RPMI Medium 1640, fetal bovine serum, Hanks' Balanced Salt Solution and other cell culture reagents were purchased from Life Technologies, Inc. (Grand Island, NY). Bovine serum albumin (BSA), pertussis toxin, and HEPES were from Sigma Chemical Co. (St. Louis, Mo.). Fura-2AM and BAPTA/AM were obtained from Molecular Probes (Eugene, Oreg.). Myo-[2-$^3$H]inositol (specific activity 10-20 Ci/mmol) was purchased from American Radiolabeled Biochemicals (St. Louis. Mo.). A plasmid containing the RAP cDNA was a kind gift from Dr. Joachim Herz, the University of Texas, Southwestern, Dallas Tex. It was used to produce RAP as previously described [21]. Human recombinant apoE2 was obtained commercially from Panvera Corp (Madison, Wis.). The preparation was free of endotoxin, and homogenous as judged by SDS-polyacrylamide gel electrophoresis. [$^3$H] thymidine (specific activity, 70 Ci/mmol) and Iodine-125 (specific activity: 440 mCi/mg) were purchased from the American Radiolabeled Chemicals, Inc. (St. Louis MO). The 20 amino acid ApoE mimetic peptide (Ac-TEELRVR-LASHLRKLRKRLL-amide) with and without a tyrosine on the amino terminus as well as a scrambled control peptide of identical size, amino acid composition, and purity were synthesized by QCB Biochemicals (Hopkinton, Mass.) to a purity of 95%. All amino termini were acetylated and all carboxyl termini were blocked with an amide moiety. Peptides were reconstituted in sterile isotonic phosphate buffered saline. A scrambled control peptide of identical size, amino acid composition, and purity was also synthesized. All other reagents used were of the highest quality commercially available.

Macrophage Harvesting. All experiments involving animals were first approved by the Duke Institutional Animal Care and Use Committee. Pathogen-free female C57BL/6 mice and ApoE deficient mice previously backcrossed 10 times to the C57BL/6 strain were obtained from the Jackson Laboratory (Bar Harbor, Maine). Thioglycollate-elicited peritoneal macrophages were harvested by peritoneal lavage using 10 ml of ice-cold Hanks' balanced salt solution containing 10 mM HEPES and 3.5 mM $NaHCO_3$ (HHBSS), pH 7.4. The macrophages were pelleted by centrifugation at 4° C. at ~800×g for 10 min and resuspended in RPMI 1640 media supplemented with 25 mM HEPES, 12.5 U/ml penicillin, 6.5 mg/ml streptomycin, and 5% fetal bovine serum. Cell viability was determined by the trypan blue exclusion method and was consistently greater then 95%.

Receptor Binding Studies. Macrophages were plated in 48-well cell culture plates (Costar) at $2.5×10^5$ cells per well and incubated for 3 h at 37° C. in a humidified 5% $CO_2$ incubator. The plates were then cooled to 4° C. and unbound cells were removed by three consecutive rinses with ice-cold Hanks' balanced salt solution containing 20 mM Hepes and 5% BSA, pH 7.4 (binding buffer). To quantify direct binding of the $^{125}$I-apoE mimetic peptide, varying amounts of radiolabeled peptide were added to each well in the presence or absence of 200-fold molar excess of unlabeled peptide. Specific binding to cells was determined by subtracting the amount of $^{125}$I-apoE peptide bound in the presence of excess unlabeled peptide (nonspecific binding) from the amount of $^{125}$I-apoE peptide bound in the absence of excess unlabeled peptide (total binding). For competition studies, 50 nM radiolabeled peptide was added to each well in the presence or absence of varying amounts (31.25 nM -4 □M) of unlabeled ApoE2 or RAP. Cells were then incubated at 40° C. for 12-16 h. Unbound ligand was removed from the wells and the cell monolayer was rinsed three times with ice-cold binding buffer. Cells were then solubilized with 1 M NaOH, 0.5% SDS at room temperature for >5 h before the contents of each well was added to polystyrene tubes and counted in a LKB-Wallac, CliniGamma 1272 □-counter (Finland).

Measurement of $[Ca^{2+}]_i$ in apoE and peptide treated macrophage. Changes in $[Ca^{2+}]_i$ levels in Fura-2/AM treated single cells were quantified using digital imaging microscopy in accordance with known techniques. Macrophages were plated on glass coverslips sitting in 35 mm Petri dishes at a density of $1.5 \times 10^5$ cells/cm$^2$, and allowed to adhere for 2 h in a humidified 5% $CO_2$ incubator at 37° C. The non-adherent cells were aspirated and the monolayers were washed twice with HHBSS. 4 μM Fura-2/AM was incubated with the cells for thirty min in the dark at room temperature and $[Ca^{2+}]_i$ was subsequently measured using a digital imaging microscope in accordance with known techniques. After obtaining baseline measurements for 5 min, ligand (apoE, apoE mimetic peptide, or scrambled peptide) was added, and multiple $[Ca^{2+}]_i$ measurements were taken. To determine if signaling resulted from ligation of the ligand to LRP, cells were preincubated with a 1000-fold molar excess of RAP or 10 mM $NiCl_2$, both of which inhibit ligand binding to LRP, for 5 min prior to stimulation with apoE or peptide. In experiments in which the involvement of a G protein was assessed, monolayers were incubated with 1 μg/ml pertussis toxin for 12 h at 37° C. and $Ca^{2+}$ measurements were made as stated above.

Measurement of $IP_3$ in apoE treated macrophage and effect of pertussis toxin. The formation of $IP_3$ in myo-[2-$^3$H]inositol-labeled macrophages under various experimental conditions was quantified in accordance with known techniques. Macrophage were plated in 6 well plates ($4\times10^6$ cells/well) and allowed to adhere at 37° C. for 2 h in a humidified 5% $CO_2$ incubator. Medium was aspirated from the monolayers and RPMI 1640 medium containing 0.25% BSA and myo-[2-$^3$H]inositol (specific activity 10-20 Ci/mmol) was added to each well. The cells were incubated at 37° (C. for an additional 16-18 h. Monolayers were rinsed three times with 25 mM HHBSS containing 1 mM $CaCl_2$, 1 mM $MgCl_2$, 10 mM LiCl, pH 7.4. A volume of 0.5 ml of this solution was added to each well, and the cells were preincubated for 3 min at 37° C. before stimulated with ligand. The reaction was stopped by aspirating the medium containing the ligand and adding 6.25% perchloric acid. The cells were scraped out of the wells, transferred to tubes containing 1 ml of octylamine/Freon (1:1 vol/vol) and 5 mM EDTA, and were centrifuged at 5600×g for 20 min at 4° C. The upper phase solution was applied to a 1ml Dowex resin column (AG1-X8 formate; Bio Rad Laboratories, Richmond, CA) and eluted sequentially in batch process with $H_2O$, 50, 200, 400, 800, and 1200 mM ammonium formate containing 0.1 M formic acid [26]. Radioactivity was determined by placing aliquots in a liquid scintillation counter to determine radioactivity. To evaluate the pertussis-toxin sensitivity of the G protein coupled to receptor activation and phosphatidyl inositol 4,5-bisphosphate (PIP2) hydrolysis, cells were plated as described above and incubated with 1 μg/ml pertussis toxin which had been preactivated with 40 mM DTT at 30° C. for 20 min. The effect on $IP_3$ formation was measured as described above.

Figure 8:
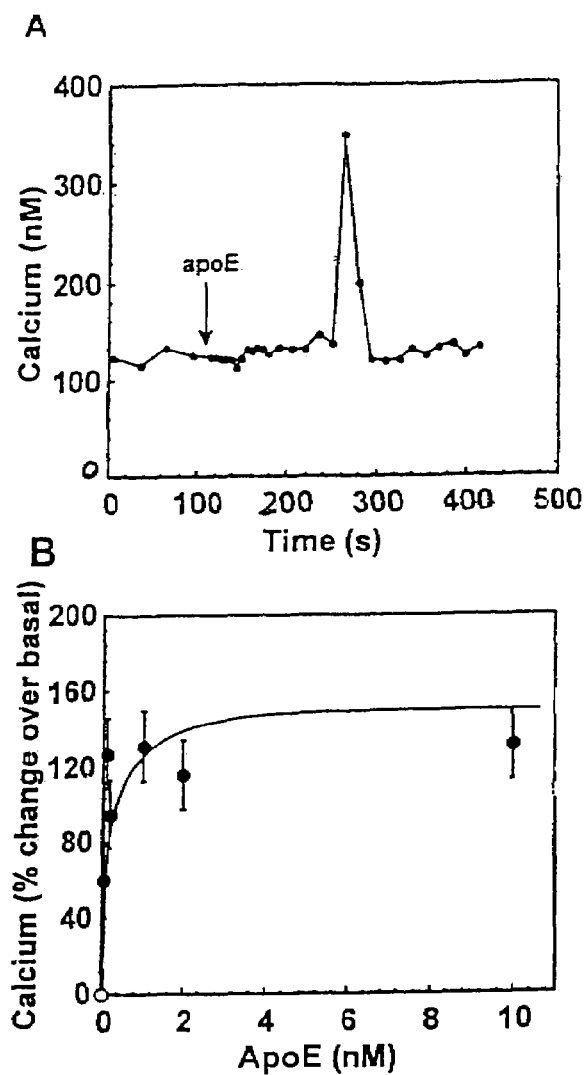
FIG. 8. Changes in $[Ca^{2+}]_i$ in macrophages treated with apoE. Panel A: Changes in $[Ca^{2+}]_i$ in a single Fura-2/AM loaded peritoneal macrophage on stimulation with apoE (100 pM). Details for measuring $[Ca^{2+}]_i$ are described in the Examples below. The graph shown is representative of 5 individual experiments using 20-30 cells each. Approximately 70-80% of the macrophage demonstrated changes in $[Ca^{2+}]_i$ upon stimulation with apoE. The arrow indicates the time of addition of apoE. Panel B: Effect of apoE concentration on changes in $[Ca^{2+}]_i$. The changes in $[Ca^{2+}]_i$ in individual cells were measured prior to and following exposure to varying concentrations of apoE. The data are displayed as mean (S.E. and are representative of two independent experiments; in each case 25-30 cells were analyzed cells per study.

Competition between apoE and apoE mimetic peptide for binding site on the receptor. Changes in macrophage $[Ca^{2+}]_i$ upon stimulation with apoE and apoE-mimetic peptide were studied to determine whether these ligands bind to the same receptor. Fura-2/AM loaded macrophages were incubated overnight, plated on glass cover slips, stimulated with one ligand, and changes in $[Ca^{2+}]_i$ quantified. Cells were then stimulated with second ligand and $Ca^{2+}$ measurements repeated B. Results Effect of apoE on macrophage $[Ca^{2+}]_i$. Modulation of free cytoplasmic $Ca^{2+}$ concentration is a ubiquitous signaling response. In many cell types, binding of ligands to plasma membrane receptors activates the hydrolysis of $PIP_2$ by membrane-bound phospholipase C, generating $IP_3$. $IP_3$ causes the release of $Ca^{2+}$ from the endoplasmic reticulum by binding to its cognate receptor, which is also a $Ca^{2+}$ channel. In non-excitable cells, $[Ca^{2+}]_i$ signaling is associated both with $Ca^{2+}$ release from intracellular stores and Ca influx. Treatment of macrophages with human recombinant apoE increased $[Ca^{2+}]_i$ levels 2-4-fold compared to macrophage treated with buffer (FIG. 8A). In a typical experiment $[Ca^{2+}]_i$ levels in unstimulated cells and apoE-treated cells were 95.33±7.37 and 180.25±14.57 nM, respectively. The increase in $[Ca^{2+}]_i$ upon stimulation with apoE was observed in 70-80% of the cells examined. ApoE-induced increase in $[Ca^{2+}]_i$ was heterogeneous, asynchronous, and either oscillatory or sustained. ApoE-induced increases in macrophage $[Ca^{2+}]_i$ was dose-dependent (FIG. 8B). To address the possibility that native apoE secreted by macrophage altered responses to exogenous human recombinant apoE, these experiments were repeated using macrophage prepared from apoE deficient mice. Calcium responses following stimulation with apoE were identical in wild-type macrophages and macrophages from apoE deficient mice (data not shown).

Figure 9A:
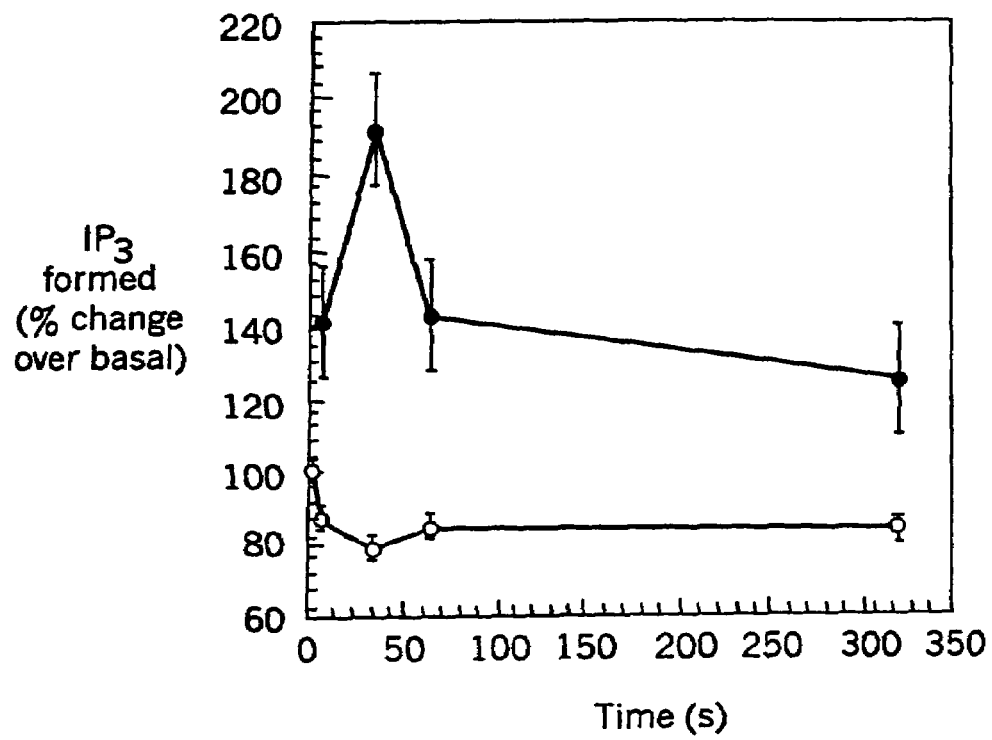
FIG. 9. Changes in $IP_3$ in macrophages treated with apoE. Panel A: Effect of apoE on $IP_3$ synthesis in macrophages, and modulation by pertussis toxin. These results are representative of two independent experiments performed in duplicate and expressed as % change in $IP_3$ formation at different time periods in myo-$[2-^3H]$ inositol-labeled cells stimulated with apoE (100 pM) in the presence (open circles) and absence (filled circles) of pertussis toxin. Panel B: Effect of apoE concentration on $IP_3$ formation in $[^3H]$ labeled macrophages. The cells were stimulated with varying concentrations of apoE for 60s and $IP_3$ determined. Results are displayed as mean (S.E. and are representative of two individual experiments performed in duplicate.
Figure 9B:
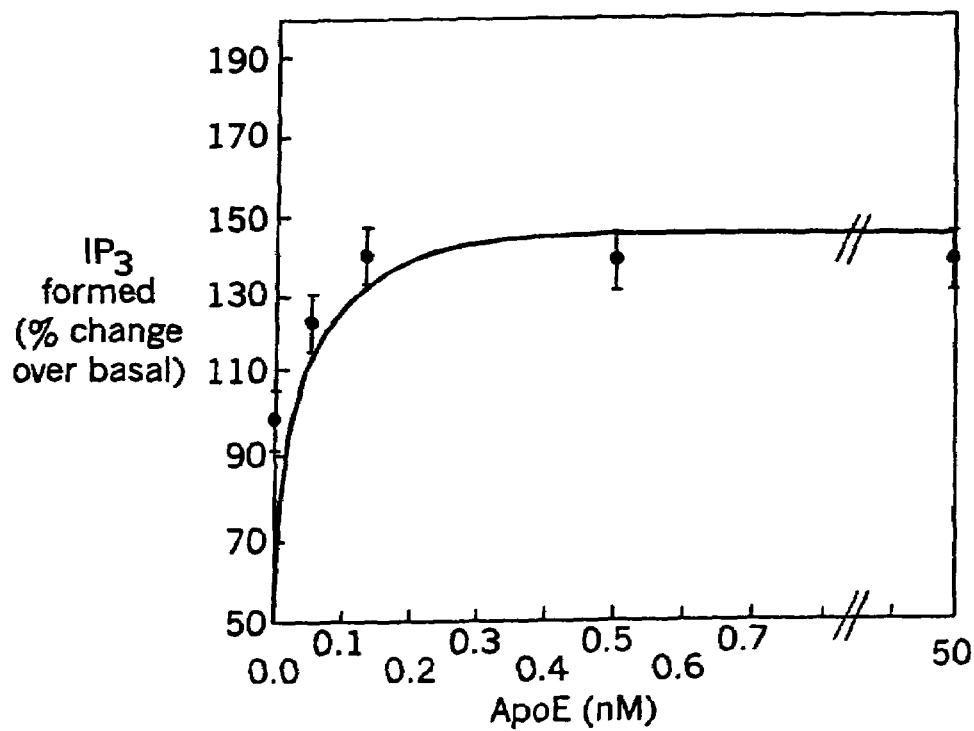

The effect of pertussis toxin on apoE-induced $IP_3$ synthesis. Exposure of myo-[2-$^3$H] inositol-labeled macrophage to apoE caused a 1.5-2.0-fold increase in $IP_3$ levels (FIG. 9A). This effect was dose-dependent (FIG. 9B). Pretreatment of the macrophages with pertussis toxin completely abolished this increase in $IP_3$. (FIG. 9A). These studies demonstrate that the phospholipase C-catalyzed hydrolysis of membrane $PIP_2$ in apoE stimulated cells is coupled to a pertussis toxin-sensitive G protein.

ApoE-induced increases in macrophage $[Ca^{2+}]_i$ are attenuated by $Ni^{2+}$ and RAP. Previous studies have demonstrated that ApoE binds to LRP and is then internalized. Additionally, binding of lactoferrin, *Pseudomonas* exotoxin A, lipoprotein lipase and thrombospondin to LRP initiates a signaling cascade associated with the generation of second messengers. To investigate the possibility that LRP is involved in the signal cascade induced by apoE, macrophages were preincubated with RAP and $Ni^{+2}$ prior to stimulation with apoE2 or apoE2 mimetic peptide. RAP is a 39 kD protein that blocks the binding of all known ligands to LRP. $Ni^{2+}$ also blocks ligand interactions with LRP. Both preincubation with RAP and $Ni^{+2}$ markedly attenuated the $[Ca^{2+}]_i$ increases associated with subsequent exposure to apoE (data not shown). These results are consistent with the hypothesis that apoE induces a signaling cascade via specific interaction with LRP. Pretreatment of macrophage with pertussis toxin also markedly attenuated the ApoE-dependent $Ca^{2+}$ response, indicating that signal transduction induced by apoE is coupled to a pertussis toxin-sensitive G protein. This is consistent with the known properties of LRP-dependent signal transduction.

Effect of apoE-mimetic peptide on macrophage $[Ca^{2+}]_i$. Stimulation of macrophage with the peptide derived from residues 130-149 of the apoE receptor binding region also resulted in a 2-3-fold increase in $[Ca^{2+}]_i$ whereas a scrambled control peptide of identical size and composition had no effect (data not shown). This increase in $[Ca^{2+}]_i$ was observed in approximately 60-70% of cells examined. As with the apoE responses, peptide-induced increases in macrophage $[Ca^{2+}]_i$ were heterogeneous and asynchronous. These results demonstrate that both intact apoE and a peptide derive from the apoE receptor binding region induce an increase in $[Ca^{2+}]_i$ that is consistent with the initiation of a signaling cascade. However, on a molar basis, higher concentrations of peptide were necessary to get $[Ca^{2+}]_i$ responses compared to the intact apoE. This difference likely results from differences in receptor affinity between the peptide and apoE, a property generally seen when comparing the effects of intact proteins to peptide ligands.

Effects of repeated stimulation of apoE and apoE-mimetic peptide on $[Ca^{2+}]_i$. We evaluated the possibility of competition between apoE and its mimetic peptide for binding sites on the receptor by quantifying the changes in $[Ca^{2+}]_i$ consequent to receptor ligation. Following repeated exposure to apoE, there was a marked attenuation in $[Ca^{2+}]_i$ suggesting tachyphylaxis (data not shown). Following the increase in $[Ca^{2+}]_i$ associated with the initial exposure to human recombinant apoE, there was a marked attenuation in $[Ca^{2+}]_i$ response to subsequent peptide exposure (data not shown). Similarly, there was a loss of $[Ca^{2+}]_i$ response to apoE addition following initial exposure to peptide (data not shown). No desensitization in calcium response was observed with exposure of scrambled peptide (data not shown). This observed tachyphylaxis suggests receptor desensitization secondary to receptor ligation, and is consistent with the hypothesis that both the intact apoE protein and the 20 residue peptide bind to the same receptor.

C. Discussion

The primary observations of this example are that: 1) binding to receptors on the macrophage cell surface of human recombinant apoE (in pM to nM concentrations) initiates signaling events associated with increases in $[Ca^{2+}]_i$ and $IP_3$; 2) a 20 residue peptide derived from the receptor binding region of apoE, but not a scrambled control peptide, causes identical changes in macrophage $[Ca^{2+}]_i$; 3) changes in $[Ca^{2+}]_i$ and $IP_3$ are specific and dose-dependent; 4) apoE-induced increase in cellular $IP_3$ is pertussis toxin-sensitive; and 5) changes in $[Ca^{2+}]_i$ are blocked by RAP and $Ni^{2+}$. Moreover, based on the presence of cross-desensitization, apoE and the apoE-mimetic peptide appear to bind to the same receptor.

EXAMPLE 11

An Apolipoprotein E Mimetic Peptide is

Protective in a Murine Head Injury Model

This Example demonstrates a protective effect of intravenous administration of a 17 amino acid ApoE mimetic peptide (the fragment of ApoE containing nucleic acids 133-149) (SEQ ID No.:10)) following head injury.

Mice were endotracheally intubated and their lungs were mechanically ventilated with 1.6% isoflurane at 30% partial pressure of oxygen. The mice received a midline closed head injury delivered by a pneumatic impactor at a speed of 6.8 m/s. Thirty minutes after closed head injury, mice were randomized into 3 groups (n=16 mice per group as follows: high dose peptide (406 ug/kg), low dose peptide (203 ug/kg), and saline control solution. All peptide solutions were prepared in sterile isotonic saline (100 ul) and delivered intravenously via tail vein injection. Rotorod time and weight were measured for five consecutive days after injury. At 21 days, the ability to learn to find a hidden platform in the Morris Water Maze was tested.

Figure 10:
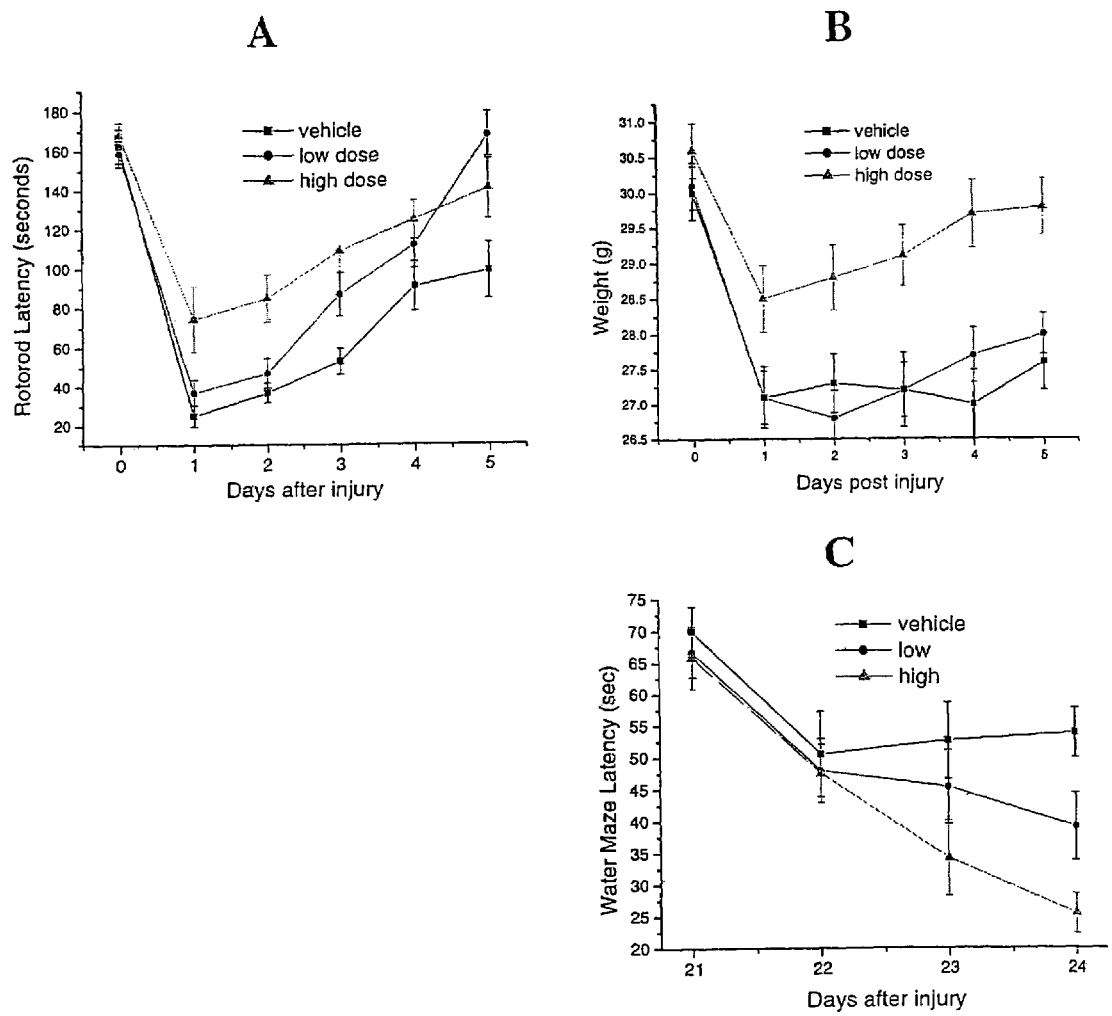
FIG. 10A shows the performance of mice with and without treatment on rotorod latency after closed head injury.
FIG. 10B shows the weight gain of mice with and without treatment after closed head injury.
FIG. 10C shows the performance of mice with and without treatment in a water maze latency test after closed head injury.

Prior to injury, rotorod latency and weights were comparable in all animals. After injury, the saline injected animals had a profound deficit in rotorod testing which was associated with weight loss. High dose peptide, and to a lesser extent low dose peptide protected animals from this motor deficit (FIG. 10A), and concomitant weight loss (FIG. 10b). This protective effect of the single dose of peptide was sustained for five days following injury (p<0.05 3-way repeat measures ANOVA).

In addition, the peptide appeared to provide protection in learning deficits in learning to find a hidden platform (FIG. 10C) in the Morris Water Maze (p<0.05 3-way repeat measures ANOVA). Treatment with the peptide also resulted in a significant improvement in acute survival as demonstrated by Kaplan-Meier analysis (data not shown).

The foregoing examples are illustrative of the present invention, and are not to be construed as limiting thereof. The invention is described by the following claims, with equivalents of the claims to be included therein.

That which is claimed is:

1. An isolated peptide consisting of the sequence of SEQ ID No.: 10.

2. A composition comprising a peptide consisting of the peptide of claim 1 in combination with a pharmaceutically acceptable carrier, diluent or excipient.

3. The composition of claim 2, wherein said peptide is conjugated to a carrier molecule that increases transport of said peptide across the blood-brain barrier, compared to that which would occur in the absence of said carrier molecule.

4. The composition of claim 2, wherein said carrier is selected from the group consisting of pyridinium, fatty acids, inositol, cholesterol, glucose derivatives, hemoglobin, lysozyme, cytochrome c, ceruloplasmin calmodulin ubiquitin, substance P, histone, insulin and transferrin and peptides thereof, lipid vesicles and liposomes.

5. The peptide of claim 1, wherein said peptide suppresses microglial activation.

* * * * *